(12) United States Patent
Fioretos et al.

(10) Patent No.: US 10,005,842 B2
(45) Date of Patent: *Jun. 26, 2018

(54) METHOD OF TREATMENT FOR LEUKEMIA USING AN ANTI-IL1RAP ANTIBODY

(71) Applicant: CANTARGIA AB, Lund (SE)

(72) Inventors: Thoas Fioretos, Lund (SE); Marcus Järås, Lund (SE)

(73) Assignee: Cantargia AB, Lund (SE)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/242,242

(22) Filed: Aug. 19, 2016

(65) Prior Publication Data

US 2017/0198048 A1 Jul. 13, 2017

Related U.S. Application Data

(63) Continuation of application No. 13/390,459, filed as application No. PCT/GB2010/001612 on Aug. 20, 2010, now Pat. No. 9,458,237.

(60) Provisional application No. 61/272,146, filed on Aug. 21, 2009, provisional application No. 61/296,143, filed on Jan. 19, 2010.

(30) Foreign Application Priority Data

Aug. 21, 2009 (GB) .................................. 0914644.0

(51) Int. Cl.
| | |
|---|---|
| C07K 16/28 | (2006.01) |
| C07K 16/30 | (2006.01) |
| A61K 39/00 | (2006.01) |
| G01N 33/574 | (2006.01) |
| C12Q 1/68 | (2018.01) |

(52) U.S. Cl.
CPC ...... *C07K 16/2866* (2013.01); *C07K 16/3061* (2013.01); *C12Q 1/6886* (2013.01); *G01N 33/57426* (2013.01); *C07K 2317/73* (2013.01); *C07K 2317/732* (2013.01); *C07K 2317/76* (2013.01); *C12Q 2600/158* (2013.01); *G01N 2333/7155* (2013.01)

(58) Field of Classification Search
None
See application file for complete search history.

(56) References Cited

U.S. PATENT DOCUMENTS

| | | | |
|---|---|---|---|
| 4,235,871 | A | 11/1980 | Papahadjopoulos et al. |
| 4,816,567 | A | 3/1989 | Cabilly et al. |
| 5,120,525 | A | 6/1992 | Goldenberg |
| 5,851,451 | A | 12/1998 | Takechi et al. |
| 6,068,830 | A | 5/2000 | Diamandis |
| 6,280,955 | B1 | 8/2001 | Cao |
| 8,715,619 | B2 | 5/2014 | Karsunky |
| 2003/0026806 | A1 | 2/2003 | White et al. |
| 2003/0170632 | A1 | 9/2003 | Sims et al. |
| 2003/0215453 | A1 | 11/2003 | Dedera et al. |
| 2007/0071675 | A1 | 3/2007 | Wu et al. |
| 2007/0154931 | A1 | 7/2007 | Radich et al. |
| 2008/0280774 | A1 | 11/2008 | Burczynski et al. |
| 2017/0121420 | A1 | 5/2017 | Heidrich et al. |

FOREIGN PATENT DOCUMENTS

| | | |
|---|---|---|
| EP | 0 213 303 | 3/1987 |
| EP | 0213303 | 3/1987 |
| GB | 0914644.0 | 2/2011 |
| WO | 1996/023067 | 8/1996 |
| WO | 2003/014309 | 2/2003 |
| WO | 2004/100987 | 11/2004 |
| WO | 2005005601 | 1/2005 |
| WO | 2006/110593 | 10/2006 |
| WO | 2007/024715 | 3/2007 |
| WO | 2007/112097 | 10/2007 |
| WO | 2009091547 A1 | 7/2009 |
| WO | 2009/120899 | 10/2009 |
| WO | 2009/120903 | 10/2009 |
| WO | 2016207304 A2 | 12/2016 |
| WO | 2017079121 A2 | 5/2017 |

OTHER PUBLICATIONS

Raman Mocharla et al. (1989) Immunological Investigations, 18(5) pp. 689-696, entitled "Polyanions Inhibit Murine Macrophage Fc Receptor Mediated ADCC and Binding".

Dolph O. Adams et al. (Jun. 1984) Proc. Natl. Acad. Sci. USA vol. 81 pp. 3506-3510, Immunology entitled "Tumors undergoing rejection induced by monoclonal antibodies of the IgG2a isotype contain increased numbers of macrophages activated for a distinctive form of antibody-dependent cytolysis".

Balagurunathan, Y., et al., "Gene expression profiling-based identification of cell-surfae targets for developing miltimetric ligands in pancreatic cancer," Mol. Cancer Ther., Sep. 2008, 7(9), pp. 3071-3080.

(Continued)

*Primary Examiner* — Elly-Gerald Stoica

(74) *Attorney, Agent, or Firm* — McNeill Baur PLLC

(57) ABSTRACT

The present invention provides agents comprising or consisting of a binding moiety with specificity for interleukin-1 receptor accessory protein (IL1RAP) for use in inducing cell death and/or inhibiting the growth and/or proliferation of pathological stem cells and/or progenitor cells associated with a neoplastic hematologic disorder, wherein the cells express IL1RAP. A related aspect of the invention provides agents comprising or consisting of a binding moiety with specificity for interleukin-1 receptor accessory protein (IL1RAP) for use in detecting pathological stem cells and/or progenitor cells associated with a neoplastic hematologic disorder, wherein the cells express IL1RAP. Further provided are pharmacological compositions comprising the agents of the invention and methods of using the same.

14 Claims, 15 Drawing Sheets

(56) References Cited

OTHER PUBLICATIONS

Figure 1:
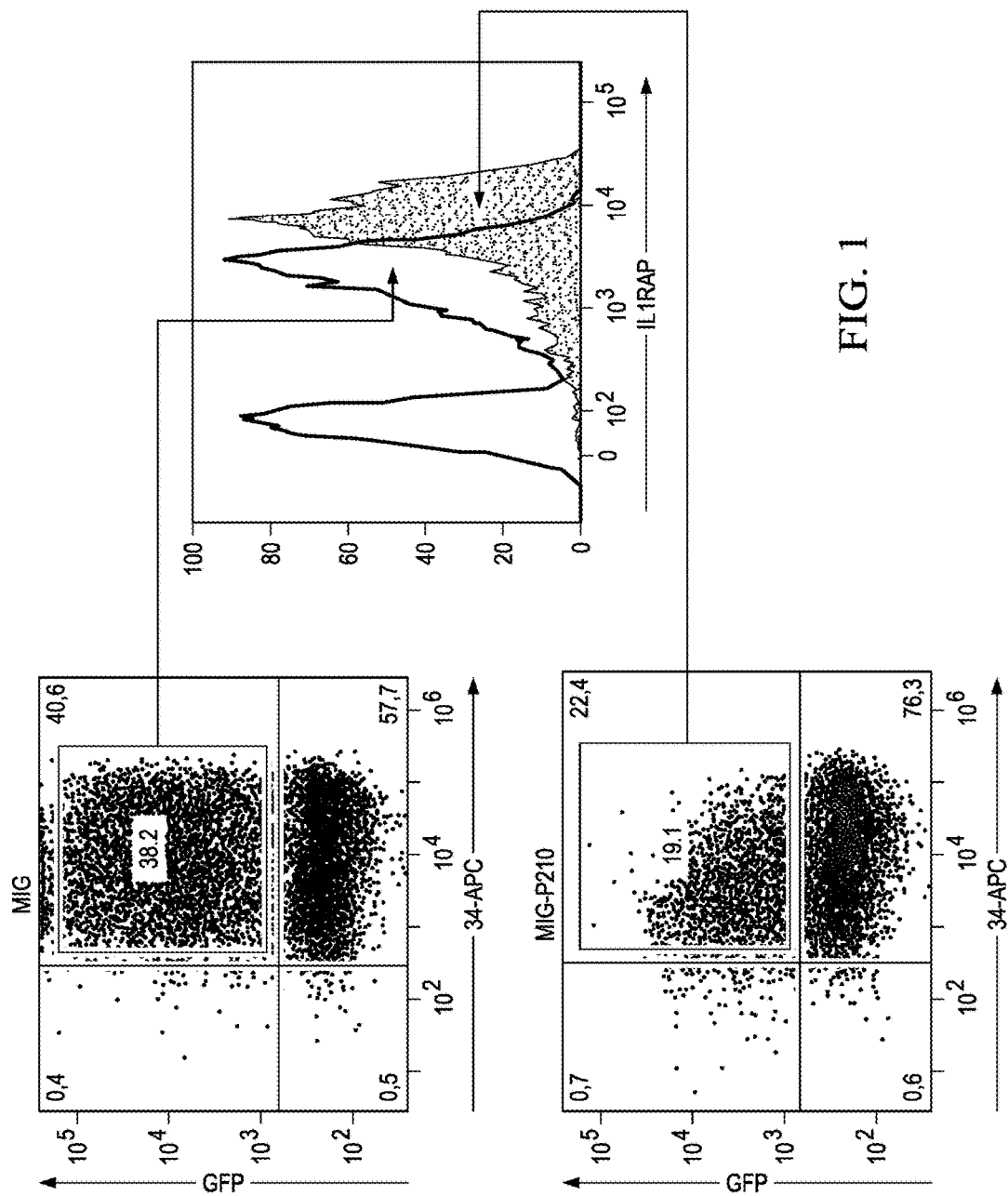

Jaras, M. et al., "Isolation and killing at candidate chronic myeloid leukemia stem cells by antibody targeting of IL-1 receptor accessory protein," Proc Natl Acad Sci USA, Sep. 14, 2010, 107(37), pp. 16280-16285.
Jensen, L., et al., "IL-1 Signaling Cascasde in Liver Cells and the Involvement of a Soluble Form of the IL-1 Receptor Accessory Protein", The Journal of Immunology, 2000, vol. 164, pp. 5277-5286.
Ilyinm, S., et al., "Brain tumor development in rats is associated with changes in central nervous system cytokine and neuropeptide systems", Brain Research Bulletin, 1999, vol. 48:4, pp. 363-373.
Riechmann, L., et al., "Reshaping human antibodies for therapy," Nature, Mar. 24, 1988, 332(6162), pp. 323-327.
Van Rhenen, A., et al., "The novel AML stem cell associated antigen CLL-1 aids in discrimination between normal and leukemic stem cells," Blood, Oct. 1, 2011, 110(7), pp. 2659-2666.
Wilkinson, R.W., et al., "Antibody-dependent cell-mediated cytoxicity: a flow cytometry-based using flurophores," J Immunol Methods, Dec. 1, 2001, 258(1-2), pp. 183-191.
Winter, G., et al., "Man-made antibodies," Nature, Jan. 24, 1991, 349(6307), pp. 293-299.
Thaczuk, K., et al., "Review of the Contemporary Cytotoxic and Biologic Combinations Available for the Treatment of Metastatic Breast Cancer," Clinical Therapeutics, Sep. 24, 2009, vol. 31, pp. 2273-2289.
Roitt, et al, "Immunology: Antibodies and their Receptors," Times Mirror International Publishers Limited, 1996, 26 pages.
Ali, S., et al. "IL-1 receptor accessory protein is essential for IL-33-induced activation of T lymphocytes and mast cells." Proc Natl Acad Sci U S A. Nov. 20, 2007;104(47):18660-5. Epub Nov. 14, 2007.
Bhatia, M., et al. "Purification of primitive human hematopoietic cells capable of repopulating immune-deficient mice." Proc Natl Acad Sci U S A. May 13, 1997;94(10):5320-5.
Boerner, P., et al. "Production of antigen-specific human monoclonal antibodies from in vitro-primed human splenocytes." J Immunol. Jul. 1, 1991;147(1):86-95.
Bunka, D.H., et al. "Aptamers come of age—at last." Nat Rev Microbiol. Aug. 2006;4(8):588-96.
Castor, A., et al. "Distinct patterns of hematopoietic stem cell involvement in acute lymphoblastic leukemia." Nat Med. Jun. 2005;11(6):630-7. Epub May 22, 2005.
Cole, S.P., et al. "Human monoclonal antibodies." Mol Cell Biochem. Jun. 1984;62(2):109-20.
Cole, S.P., et al. "The EBV-Hybridoma Technique and its Application to Human Lung Cancer." In Monoclonal Antibodies and Cancer Therapy, R.A. Reisfeld & S. Sell, eds. Jan. 1985;77-96.
Copland, M., et al. "Dasatinib (BMS-354825) targets an earlier progenitor population than imatinib in primary CML but does not eliminate the quiescent fraction." Blood. Jun. 1, 2006;107(11):4532-9. Epub Feb. 9, 2006.
Cote, R.J., et al. "Generation of human monoclonal antibodies reactive with cellular antigens." Proc Natl Acad Sci U S A. Apr. 1983;80(7):2026-30.
Cullinan, E.B., et al. "IL-1 receptor accessory protein is an essential component of the IL-1 receptor." J Immunol. Nov. 15, 1998;161(10):5614-20.
Deininger, M.W., et al. "The molecular biology of chronic myeloid leukemia." Blood. Nov. 15, 2000;96(10):3343-56.
Dick, J.E. "Stem cell concepts renew cancer research." Blood. Dec. 15, 2008;112(13):4793-807.
Drabovich, A.P., et al. "Selection of smart aptamers by methods of kinetic capillary electrophoresis." Anal Chem. May 1, 2006;78(9):3171-8.
Eisterer, W., et al. "Different subsets of primary chronic myeloid leukemia stem cells engraft immunodeficient mice and produce a model of the human disease." Leukemia. Mar. 2005;19(3):435-41.
Ema, H., et al. "Adult mouse hematopoietic stem cells: purification and single-cell assays." Nat Protoc. 2006;1(6):2979-87.

Estrov, Z., et al. "Suppression of chronic myelogenous leukemia colony growth by interleukin-1 (IL-1) receptor antagonist and soluble IL-1 receptors: a novel application for inhibitors of IL-1 activity." Blood. Sep. 15, 1991;78(6):1476-84.
Fialkow, P.J., et al. "Chronic myelocytic leukemia. Origin of some lymphocytes from leukemic stem cells." J Clin Invest. Oct. 1978;62(4):815-23.
Fields, S., et al. "A novel genetic system to detect protein-protein interactions." Nature. Jul. 20, 1989;340(6230):245-6.
GenBank Accession AAB84059. "IL-1 receptor accessory protein [Homo sapiens]." (accessed May 4, 2012).
Graham, S.M., et al. "Primitive, quiescent, Philadelphia-positive stem cells from patients with chronic myeloid leukemia are insensitive to STI571 in vitro" Blood. Jan. 1, 2002;99(1):319-25.
Guo, W., et al. "Multi-genetic events collaboratively contribute to Pten-null leukaemia stem-cell formation." Nature. May 22, 2008;453(7194):529-33. Epub May 7, 2008.
Henikoff, J.G., et al. "Epigenome characterization at single base-pair resolution." Proc Natl Acad Sci U S A. Nov. 8, 2011;108(45):18318-23. Epub Oct. 24, 2011.
Hogge, D.E., et al. "Enhanced detection, maintenance, and differentiation of primitive human hematopoietic cells in cultures containing murine fibroblasts engineered to produce human steel factor, interleukin-3, and granulocyte colony-stimulating factor." Blood. Nov. 15, 1996;88(10):3765-73.
Hoogenboom, H.R., et al. "By-passing immunisation. Human antibodies from synthetic repertoires of germline VH gene segments rearranged in vitro." J Mol Biol. Sep. 20, 1992;227(2):381-8.
Hoppe-Seyler, F., et al. "Peptide aptamers: powerful new tools for molecular medicine." J Mol Med (Berl). 2000;78(8):426-30.
Hosen, N., et al. "CD96 is a leukemic stem cell-specific marker in human acute myeloid leukemia." Proc Natl Acad Sci U S A. Jun. 26, 2007;104(26):11008-13. Epub Jun. 18, 2007.
Huang, J., et al. "Recruitment of IRAK to the interleukin 1 receptor complex requires interleukin 1 receptor accessory protein." Proc Natl Acad Sci U S A. Nov. 25, 1997;94(24):12829-32.
Hystad, M.E., et al. "Characterization of early stages of human B cell development by gene expression profiling." J Immunol. Sep. 15, 2007;179(6):3662-71.
Jaras, M., et al. "Adenoviral vectors for transient gene expression in human primitive hematopoietic cells: applications and prospects." Exp Hematol. Mar. 2007;35(3):343-9.
Jaras, M., et al. "Expression of P190 and P210 BCR/ABL1 in normal human CD34(+) cells induces similar gene expression profiles and results in a STAT5-dependent expansion of the erythroid lineage." Exp Hematol. Mar. 2009;37(3):367-75. Epub Jan. 9, 2009.
Jiang, X., et al. "Chronic myeloid leukemia stem cells possess multiple unique features of resistance to BCR-ABL targeted therapies." Leukemia. May 2007;21(5):926-35. Epub Mar. 1, 2007.
Jiang, X., et al. "Stem cell biomarkers in chronic myeloid leukemia." Dis Markers. 2008;24(4-5):201-16.
Jin, L., et al. "Targeting of CD44 eradicates human acute myeloid leukemic stem cells." Nat Med. Oct. 2006;12(10):1167-74. Epub Sep. 24, 2006.
Jin, L., et al. "Monoclonal antibody-mediated targeting of CD123, IL-3 receptor alpha chain, eliminates human acute myeloid leukemic stem cells." Cell Stem Cell. Jul. 2, 2009;5(1):31-42.
Jones, P.T., et al. "Replacing the complementarity-determining regions in a human antibody with those from a mouse." Nature. May 29-Jun 4, 1986;321(6069):522-5.
Jorgensen, H.G., et al. "Nilotinib exerts equipotent antiproliferative effects to imatinib and does not induce apoptosis in CD34+ CML cells." Blood. May 1, 2007;109(9):4016-9. Epub Jan. 9, 2007.
Kavalerchik, E., et al. "Chronic myeloid leukemia stem cells." J Clin Oncol. Jun. 10, 2008;26(17):2911-5.
Kiel, M.J. et al. "SLAM family receptors distinguish hematopoietic stem and progenitor cells and reveal endothelial niches for stem cells." Cell. Jul. 1, 2005;121(7):1109-21.
Kohler, G., et al. "Continuous cultures of fused cells secreting antibody of predefined specificity." Nature. Aug. 7, 1975;256(5517):495-7.

(56) References Cited

OTHER PUBLICATIONS

Kozbor, D., et al. "Specific immunoglobulin production and enhanced tumorigenicity following ascites growth of human hybridomas." J Immunol Methods. Jul. 15, 1985;81(1):31-42.
Majeti, R., et al. "CD47 is an adverse prognostic factor and therapeutic antibody target on human acute myeloid leukemia stem cells." Cell. Jul. 23, 2009;138(2):286-99.
Marks, J.D., et al. "By-passing immunization. Human antibodies from V-gene libraries displayed on phage." J Mol Biol. Dec. 5, 1991;222(3):581-97.
Miller, J.S., et al. "Single adult human CD34(+)/Lin-/CD38(-) progenitors give rise to natural killer cells, B-lineage cells, dendritic cells, and myeloid cells." Blood. Jan. 1, 1999;93(1):96-106.
Morris, J.C., et al. "Antibody-based therapy of leukaemia." Expert Rev Mol Med. Sep. 30, 2009;11:e29.
NCBI reference sequence NP_002173.1. "Interleukin-1 receptor accessory protein isoform 1 precursor [Homo sapiens]." (accessed May 4, 2012).
Nilsson, M., et al. "Functionally distinct subpopulations of cord blood CD34+ cells are transduced by adenoviral vectors with serotype 5 or 35 tropism." Mol Ther. Mar. 2004;9(3):377-88.
Orlandi, R., et al. "Cloning immunoglobulin variable domains for expression by the polymerase chain reaction." Proc Natl Acad Sci U S A. May 1989;86(10):3833-7.
Plant, A.L., et al. "Phospholipid/alkanethiol bilayers for cell-surface receptor studies by surface plasmon resonance." Anal Biochem. Apr. 10, 1995;226(2):342-8.
Presta, L.G. "Antibody engineering." Curr Opin Biotechnol. Aug. 1992;3(4):394-8.
Rambaldi, A., et al. "Modulation of cell proliferation and cytokine production in acute myeloblastic leukemia by interleukin-1 receptor antagonist and lack of its expression by leukemic cells." Blood. Dec. 15, 1991;78(12):3248-53.
Riechmann, L., et al. "Reshaping human antibodies for therapy." Nature. Mar. 24, 1988;332(6162):323-7.
Skerra, A., et al. "Alternative non-antibody scaffolds for molecular recognition." Curr Opin Biotechnol. Aug. 2007;18(4):295-304. Epub Jul. 20, 2007.
Subramaniam, S., et al. "The interleukin 1 receptor family." Dev Comp Immunol. May 3, 2004;28(5):415-28.
Tavor, S., et al. "CXCR4 regulates migration and development of human acute myelogenous leukemia stem cells in transplanted NOD/SCID mice." Cancer Res. Apr. 15, 2004;64(8):2817-24.
UniProt KB/Swiss-Prot Accession No. Q9NPH3-1. "Interleukin-1 receptor accessory protein." (accessed May 4, 2012).
Van Rhenan, A., et al. "The novel AML stem cell associated antigen CLL-1 aids in discrimination between normal and leukemic stem cells." Blood. Oct. 1, 2007;110(7):2659-66. Epub Jul. 3, 2007.
Verhoeyen, M., et al. "Reshaping human antibodies: grafting an antilysozyme activity." Science. Mar. 25, 1988;239(4847):1534-6.
Wilkinson, R.W., et al. "Antibody-dependent cell-mediated cytotoxicity: a flow cytometry-based assay using fluorophores." J Immunol Methods. Dec. 1, 2001;258(1-2):183-91.
Winter, G., et al. "Man-made antibodies." Nature. Jan. 24, 1991;349(6307):293-9.
Majeti, R., et al. "CD47 is an adverse prognostic factor and therapeutic antibody target on human acute myeloid leukemia stem cells." Cell. Jul. 23;138(2):286-99.
Dolph O. Adams et al. (Jun. 1984) Proc. Nail. Acad. Sci. USA vol. 81 pp. 3506-3510, Immunology entitled "Tumors ndergoing rejection induced by monoclonal antibodies of the IgG2a isotype contain increased numbers of macrophages activated for a distinctive fonm of anitibody-dependent cytolysis".
Juric, D. et al. (2007) J. Clin. Oneal. 25,1341-1349 entitled "Differential gene expression patterns and interaction elworks in BCR-ABL-positive and -negative adult Acute Lymphoblastic Leukemias".
Brendel, C. and Neubauer A. (2000) Leukemia 14, 1711-1717 entitled "Characteristics and analysis of normal and eukemic stem cells: current concepts and future directions".

Gal, H. et al. (2006) Leukemia 20, 2147-2154 entitled "Gene expression profiles of AML derived stem cells similarity to hiematopoietic stem cells".
Jiang, X. et al. (2007) Leukemia 21, 926-935 entitled "Chronic myeloid leukemia stem cells possess multiple unique features of resistance to BCR-ABL targeted therapies".
Ben-Kasus, T. et al. (2007) Mol Oncol. 1,42-54 entilled "Cancer therapeutic antibodies come of age: Targeting minimal residual disease".
Von Mehren, M. et al. (2003) Annu. Rev. Med. 54, 343-369 entitled "Monoclonal antibody therapy for cancer".
Lannello, A. and Ahmed, A. (2005) Cancer Metastasis Rev. 24, 487-499 entitled "Role of antibody-dependent cellmediated cytotoxicity in the efficacy of therapeutic anti-cancer monoclonal antibodies".
EPO Notice of Opposition EPO Form 2300E-BI98-00090PI; Dated: Jun. 20, 2016; 35 pages.
Balagurunathan, Y., et al., "Gene expression profiling-based identification of cell-surface targets for developing miltimetric ligands in pancreatic cancer," Mol. Cancer Ther., Sep. 2008, 7(9), pp. 3071-3080.
Jaras, M. et al., "Isolation and killing of candidate chronic myeloid leukemia stem cells by antibody targeting of IL-1 receptor accessory protein," Proc Natl Acad Sci USA, Sep. 14, 2010, 107(37), pp. 16280-16285.
Wilkinson, R.W., et al., "Antibody-dependent cell-mediated cytoxicity: a flow cytometry-based using flurophores," J Immunol Methods, Dec. 1, 2001, 258{1-2), pp. 183-191.
Roitt, et al., "Immunology: Antibodies and their Receptors," Times Mirror International Publishers Limited, 1996,26 pages.
Strome. S.E .. et al. "A mechanistic perspective of monoclonal antibodies in cancer therapy beyond target-related effects." Oncologist. Sep. 2007;12(9):1084-95.
Subramaniam, S., et al. "The interleukin 1 receptor family." Dev Camp Immunol. May 3, 2004;213(5):415-2B.
Visvader. J.E .. et al. "Cancer stem cells in solid tumours: accumulating evidence and unresolved questions." Nat Rev Cancer. Oct. 200B ;8(10):755-68. E.pub Sep. 11, 2008.
Ali, S., et al. "IL-1 receptor accessory protein is essential for IL-33-induced activation of T lymphocytes and mast cells." Proc Natl Acad Sci USA. Nov. 20, 2007;104(47):18660-5. Epub Nov. 14, 2007.
Bhatia. M. et al. "Purification of primitive human hematopoietic cells capable of repopulating immune-deficient mice." Proc Natl Acad Sci USA. May 13, 1997;94(10):5320-5.
Boerner. P., et al. "Production of antigen-specific human monoclonal antibodies from in vitro-primed human splenocytes." J Immunol. Jull. 1991;147(1):86-95.
Bunka, D.H., et al. "Aptamers come of age—at las!." Nat Rev Microbial. Aug. 2006;4(8):588-96.
Copland, M., et al. "Dasatinib (BMS-354825) targets an earlier progenitor population than imatinib in primary CML but does not eliminate the quiescent fraction." Blood. Jun. 1, 2006; 107(11 ):4532-9. Epub Feb. 9, 2006.
Cote, R.J., et al. "Generation of human monoclonal antibodies reactive with cellular antigens." Proc Natl Acad Sci USA.Apr. 1983;80(7):2026-30.
Cullinan, E.B., et al. "IL-I receptor accessory protein is an essential component of the IL-1 receptor." J Immunol. Nov. 15, 1998;161(10):5614-20.
Deininger, MW., et al. "The molecular biology of chronic myeloid leukemia." Blood. Nov. 15, 2000;96(10):3343-56.
Drabovich. A.P., et al. "Selection of smart aptamers by methods of kinetic capillary electrophoresis." Anal Chem. May 1, 2006 ;78(9):3171-8.
Ema, H., et al. "Adult mouse hematopoietic stem cells: purification and single-cell assays." Nat Protoc. 2006; 1(6):2979-87.
Estrov, Z., et al. "Suppression of chronic myelogenous leukemia colony growth by interleukin-1 (IL-1) receptor antagonist and soluble IL-1 receptors: a novel application for inhibitors of IL-1activity." Blood. Sep. 15, 1991;78(6):1476-84.

(56) References Cited

OTHER PUBLICATIONS

Graham, S.M., et al. "Primitive, quiescent, Philadelphia-positive stem cells from patients with chronic myeloid leukemia are insensitive to STI571 in vitro." Blood. Jan. 1, 2002; 99(1 ):319-25.

Guo, W., et al. "Multi-genetic events collaboratively contribute to pten-nuilleukaemia stem-cell formation." Nature. May 22, 2008;453(7194):529-33. Epub May 7, 2008.

Henikoff, J.G., et al. "Epigenome characterization at single base-pair resolution." Proc Natl Acad Sci USA. Nov. 8, 2011;108(45):18318-23. Epub Oct. 24, 2011.

Hogge, DE, et al. "Enhanced detection, maintenance, and differentiation of primitive human hematopoietic cells in cultures containing murine fibroblasts engineered to produce human steel factor, interleukin-3, and granulocyte colony-stimulating factor." Blood. Nov. 15, 1996;88(10):3765-73.

Hoogenboom. H.R. .. et al. "By-passing immunisation. Human antibodies from synthetic repertoires of germline VH gene segments rearranged in vitro." J Mol Biol. Sep. 20, 1992;227(2):381-8.

Hoppe-Seyler. F. et al. "Peptide aptamers: powerful new tools for molecular medicine." J Mol Med (Berl). 2000;78(8):426-30.

Hosen, N., et al. "CD96 is a leukemic stem cell-specific marker in human acute myeloid leukemia." Proc Natl Acad Sci USA. Jun. 26, 2007;104(26):11008-13. Epub Jun. 18, 2007.

Huang, J., et al. "Recruitment of IRAK to the interleukin 1 receptor complex requires interleukin 1 receptor accessory protein." Proc Natl Acad Sci USA. Nov. 25, 1997;94(24):12829-32.

Hystad, ME, et al. "Characterization of early stages of human B cell development by gene expression profiling."J Immunol. Sep. 15, 2007;179(6):3662-71.

Jaras, M., et al. "Expression of P190 and P210 BCRIABL 1 in normal human CD34(+) cells induces similar gene expression profiles and results in a STAT5-dependent expansion of the erythroid lineage." Exp Hematol. Mar. 2009;37(3):367-75. Epub Jan. 9, 2009.

Jiang, X., et al. "Chronic myeloid leukemia stem cells possess multiple unique features of resistance to BCR-ABL targeted therapies." Leukemia. May 2007;21 (5):926-35. Epub Mar. 1, 2007.

Jin, L., et al. "Targeting of CD44 eradicates human acute myeloid leukemic stem cells." Nat Med. Oct. 2006;12(10):1167-74. Epub Sep. 24, 2006.

Jones, PT, et al. "Replacing the complementarity-determining regions in a human antibody with those from a mouse." Nature. May 29-Jun. 4, 1986;321(6069):522-5.

Kiel, M.J., et al. "SLAM family receptors distinguish hematopoietic stem and progenitor cells and reveal endothelial niches for stem cells." Cell. Jul. 1, 2005 ;121 (7):1109-21.

Kohler, G., et al. "Continuous cultures of fused cells secreting antibody of predefined specificity." Nature. Aug. 7, 1975;256 (5517):495-7.

Kozbor, D., et al. "Specific immunoglobulin production and enhanced tumorigenicity following ascites growth of human hybridomas." J Immunol Methods. Jul. 16, 1985;81(1):31-42.

Marks, J.D., et al."By-passing immunization. Human antibodies from V-gene libraries displayed on phage." J Mol Biol. Dec. 5, 1991;222(3):581-97.

Miller, J.S., et al. "Single adult human CD34(+)/Lin-/CD38(-) progenitors give rise to natural killer cells, B-lineage cells, dendritic cells, and myeloid cells." Blood. Jan. 1, 1999 ;93(1 ):96-1 06.

Morris, J.C., et al. "Antibody-based therapy of leukaemia." Expert Rev Mol Med. Sep. 30, 2009;11 :e29.

NCBI reference sequence NP _002173.1. "Interleukin-I receptor accessory protein isoform 1 precursor [Homo sapiens]." (accessed May 4, 2012).

Nilsson. M .. et al. "Functionally distinct subpopulations of cord blood CD34+ cells are transduced byadenoviral vectors with serotype 5 or 35 tropism." Mol Ther. Mar. 2004;9(3):377-88.

Orlandi, R., et al. "Cloning immunoglobulin variable domains for expression by the polymerase chain reaction." Proc Natl Acad Sci USA. May 1989;86(10):3833-7.

Plant, AL, et al. "Phospholipid/alkanethiol bilayers for cell-surface receptor studies by surface plasmon resonance." Anal Biochem. Apr. 10, 1995;226(2):342-8.

Rambaldi, A., et al. "Modulation of cell proliferation and cytokine production in acute myeloblastic leukemia by interleukin-I receptor antagonist and lack of its expression by leukemic cells." Blood. Dec. 15, 1991;78(12):3248-53.

Riechmann. L., et al. "Reshaping human antibodies for therapy." Nature. Mar. 24, 1988;332(6162):323-7.

UniProt KB/Swiss-Prot Accession No. Q9NPH3-1. "Interleukin-I receptor accessory protein." (accessed May 4, 2012).

Van Rhenan, A., et al. "The novel AML stem cell associated antigen CLL-1 aids in discrimination between normal and leukemic stem cells." Blood. Oct. 1, 2007 ;110(7):2659-66. Epub Jul. 3, 2007.

Wilkinson, R.W., et al. "Antibody-dependent cell-mediated cytotoxicity: a flow cytometry-based assay using ftuorophores." J Immunol Methods. Dec. 1, 2001 ;258(1-2):183-91.

Juric, D. et al. (2007) J. Clin. Oneal. 25, 1341-1349 entitled "Differential gene expression patterns and interaction networks in BCR-ABL-positive and -negative adult Acute Lymphoblastic Leukemias".

Brendel, C. and Neubauer A. (2000) Leukemia 14, 1711-1717 entitled "Characteristics and analysis of normal and leukemic stem cells: current concepts and future directions".

Gal, H. et al. (2006) Leukemia 20, 2147-2154 entitled "Gene expression profiles of AML derived stem cells similarity to hemalopoietic stem cells".

Ben-Kasus, T. et al. (2007) Mol. Oncol. 1, 42-54 entitled "Cancer therapeutic antibodies come of age: Targeting minimal residual disease".

Iannello, A. and Ahmed, A. (2005) Cancer Metastasis Rev. 24, 487-499 entitled "Role of antibody-dependent cell-mediated cytotoxicity in the efficacy of therapeutic anti-cancer monoclonal antibodies".

EPO Notice of Opposition EPO Form 2300E-B198-00090P1; Dated: Jun. 20, 2016; 35 pages.

Ågerstam, H. et al. "Antibodies targeting human IL1RAP (IL1R3) show therapeutic effects in xenograft models of acute myeloid leukemia" PNAS 2015; 112(34)10786-10791.

Ågerstarn, H. et al. "IL1RAP antibodies block IL-1-induced expansion of candidate CML stem cells and mediate cell killing in xenograft models" Blood 2016; 128(23):2683-2693.

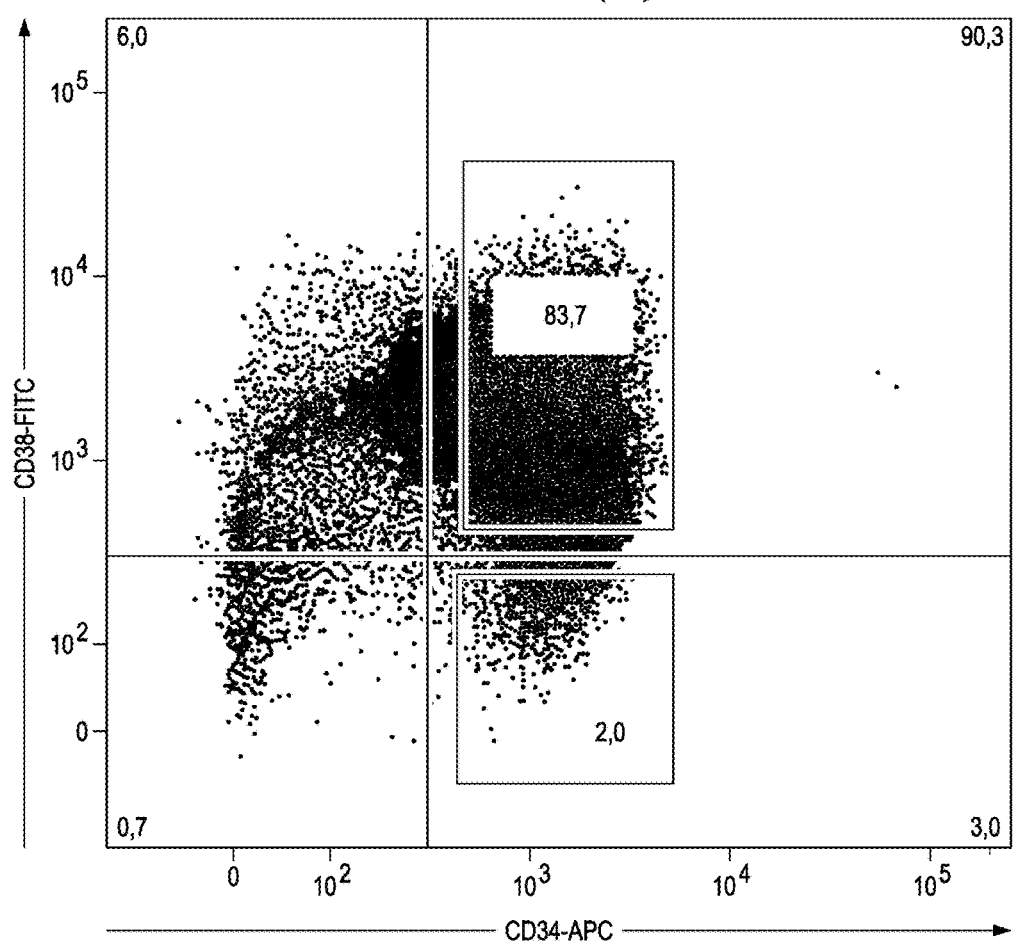

METHOD OF TREATMENT FOR LEUKEMIA USING AN ANTI-IL1RAP ANTIBODY

FIELD OF INVENTION

The present invention relates to agents for use in the treatment and diagnosis of neoplastic hematologic disorders, such as chronic myeloid leukemia (CML), acute lymphoblastic leukemia (ALL), myelodysplastic syndrome (MDS), myeloproliferative disorders (MPD) and acute myeloid leukemia (AML).

BACKGROUND

Chronic myeloid leukemia (CML) was the first human neoplasm associated with a recurrent genetic aberration; the Philadelphia (Ph) chromosome, formed through a reciprocal translocation between chromosome 9 and 22, giving rise to the constitutively active tyrosine kinase BCR/ABL1[1]. In CML, the Ph chromosome is believed to originate in a hematopoietic stem cell (HSC) as it clonally can be found both in malignant myeloid cells and non-malignant lymphoid cells[2]. The Ph chromosome is also found in a fraction of acute lymphoblastic leukemia (ALL) and acute myeloid leukemia (AML). CML is comprised of heterogeneous cell types of various maturation stages that are maintained by a small number of cells, termed CML stem cells, sharing the capacity to self-renew with normal HSC[3]. It has been demonstrated that the CML stem cells are at least partially resistant to current treatments with tyrosine kinase inhibitors[4,5], which despite clinical success show a suppressive rather than curative effect in this disorder. Thus, identifying a strategy to efficiently target CML stem cells is highly desirable to achieve a permanent cure of the disorder. Such a strategy would be to identify a target on CML stem cells that may provide novel means to eradicate the CML stem cells. Encouraging reports in this direction have been described in the related disorder acute myeloid leukemia (AML), where antibodies targeting CD123, CXCR4, CD44 or CD47 on AML stem cells show anti-leukemic effects in AML animal models[6-9]. Further, AML stem cell associated antigens such as CD96 and CLL-1 have been identified[10,11], providing additional target candidates in this disorder. Intriguingly, despite being one of the most studied neoplasms of all time, referred to as a stem cell cancer disorder, no cell surface biomarker has so far been identified in CML that allows a prospective separation of CML stem cells from normal HSCs, both residing in the rare CD34$^+$CD38$^-$ cell population[12,13]. Identification of such a biomarker would be instrumental in the characterization of the CML stem cell, but could also be used for novel treatment developments and for tracking therapeutic effects on primitive CML cells during treatment.

Accordingly, the present invention seeks to provide agents for use in the treatment and diagnosis of neoplastic hematologic disorders, such as CML. In addition, the invention seeks to provide agent for use in treatment and diagnosis of other neoplastic hematologic disorders, such as ALL, AML, Ph chromosome-negative myeloproliferative disorders (MPD), and myelodysplastic syndromes (MDS).

SUMMARY OF INVENTION

The invention provides agents for use in the treatment and/or diagnosis of neoplastic hematologic disorders and evolved directly from the discovery by the inventors that stem cells and progenitor cells associated with neoplastic hematologic disorders, such as chronic myeloid leukemia, which express IL1RAP (also known as IL1-RAP) on their surface. In contrast, normal healthy hematopoietic stem cells (as well as progenitor cells) do not express, or show very low expression levels, of IL1RAP. Moreover, the inventors have discovered that the stem and progenitor cells of other neoplastic hematologic disorders, such as ALL, AML, Ph chromosome-negative myeloproliferative disorders (MPD), and myelodysplastic syndromes (MDS), are also associated with an upregulation of IL1RAP on their cell surface. Thus, the invention provides agents for use in the treatment and/or diagnosis of neoplastic hematologic disorders associated with upregulation of IL1RAP on the surface of stem cells and/or progenitor cells.

A first aspect of the invention provides an agent comprising or consisting of a binding moiety with specificity for interleukin-1 receptor accessory protein (IL1RAP) for use in inducing cell death (either directly or indirectly via triggering of the immune system) and/or inhibiting the growth (i.e. size) and/or proliferation (i.e. number) of pathological stem cells and/or progenitor cells associated with a neoplastic hematologic disorder, wherein the stem cells and/or progenitor cells express IL1RAP. Thus, the agent may be for use in inhibiting the growth and/or proliferation of pathological stem cells alone, of progenitor cells alone, or of both pathological stem cells and progenitor cells.

The agent may also be for use in inducing differentiation of pathological stem and/or progenitor cells which express IL1RAP.

A second, related aspect of the invention provides an agent comprising or consisting of a binding moiety with specificity for interleukin-1 receptor accessory protein (IL1RAP) for use in detecting pathological stem cells and/or progenitor cells associated with a neoplastic hematologic disorder, wherein the stem cells and/or progenitor cells express IL1RAP. Thus, the agent may be for use in detecting pathological stem cells alone, progenitor cells alone, or both pathological stem cells and progenitor cells.

By "interleukin-1 receptor accessory protein", "IL1RAP" and "IL1-RAP" we specifically include the human IL1RAP protein, for example as described in GenBank Accession No. AAB84059, NCBI Reference Sequence: NP_002173.1 and UniProtKB/Swiss-Prot Accession No. Q9NPH3-1 (see also Huang et al., 1997, *Proc. Natl. Acad. Sci. USA.* 94 (24), 12829-12832). IL1RAP is also known in the scientific literature as IL1R3, C3orf13, FLJ37788, IL-1RAcP and EG3556

By "binding moiety" we include all types of chemical entity (for example, oligonucleotides, polynucleotide, polypeptides, peptidomimetics and small compounds) which are capable of binding to IL1RAP. Advantageously, the binding moiety is capable of binding selectively (i.e. preferentially) to IL1RAP under physiological conditions. The binding moiety preferably has specificity for human IL1RAP, which may be localised on the surface of a cell (e.g. the pathological stem cell or progenitor cell).

By "pathological stem cells associated with a neoplastic hematologic disorder" we include stem cells which are responsible for the development of a neoplastic hematologic disorder in an individual, i.e. neoplastic stem cells. In particular, the pathological stem cells may be leukemic stem cells (for example, as described in Guo et al., 2008, *Nature* 453(7194):529-33). Such stem cell may be distinguished from normal hematopoietic stem cells by their expression of the cell surface protein, IL1RAP (see Example below). In one embodiment, the pathological stem cells are CD34$^+$, CD38$^-$ cells By "progenitor cells" associated with a neoplastic hematologic disorder we include cells derived from pathological stem cells which are responsible for the development of a neoplastic hematologic disorder in an individual. In particular, the progenitor cells may be leukemic progenitor cells (for example, as described in Examples below; see FIG. 2b). Such progenitor cells may be distinguished from normal hematopoietic progenitor cells by their higher expression of the cell surface protein, IL1RAP (see Example below). In one embodiment, the pathological progenitor cells are CD34$^+$, CD38$^+$ cells.

By "neoplastic hematologic disorder" we specifically include hematologic cancers such as leukemias, as well as leukemia-like diseases such as myeloproliferative disorders (MPD) and myelodysplastic syndromes (MDS).

Thus, in one embodiment of the first aspect of the invention, the neoplastic hematologic disorder is a leukemic disease or disorder, i.e. a cancer of the blood or bone marrow, which may be acute or chronic.

In a further embodiment, the neoplastic hematologic disorder may be associated with cells comprising a BCR/ABL1 fusion gene. For example, the pathological stem cells and/or progenitor cells may comprise a BCR/ABL1 fusion gene.

In a related embodiment, the neoplastic hematologic disorder may be associated with cells comprising a Philadelphia (Ph) chromosome. For example, the pathological stem cells and/or progenitor cells may comprise a Ph chromosome. By "Ph chromosome" in this context we mean a specific chromosomal abnormality resulting from a reciprocal translocation between chromosome 9 and 22, specifically designated t(9;22)(q34;q11). An example of a neoplastic hematologic disorder associated with cells comprising a Ph chromosome is chronic myeloid, or myelogenous, leukemia (CML).

However, it will be appreciated by persons skilled in the art that the agents of the invention may also be used in the treatment and/or diagnosis of neoplastic hematologic disorders which are not associated with cells comprising a Philadelphia (Ph) chromosome (but nevertheless show upregulation of IL1RAP). Such neoplastic hematologic disorders which are associated with cells which do not comprise a Ph chromosome include the myelodysplastic syndromes (MDS) and myeloproliferative disorders (MPD) such as polycythemia vera (PV), essential thrombocytosis (ET) and myelofibrosis (MF).

More specifically, the neoplastic hematologic disorder may be selected from the group consisting of chronic myeloid leukemia (CML), myeloproliferative disorders (MPD), myelodysplastic syndrome (MDS), acute lymphoblastic leukemia (ALL) and acute myeloid leukemia (AML).

In one particularly preferred embodiment, the neoplastic hematologic disorder is chronic myeloid leukemia (CML).

In relation to the diagnostic aspects of the invention, it is sufficient that the agent is merely capable of binding to IL1RAP present on the surface of the pathological stem cells and/or progenitor cells (without having any functional impact upon those cells).

In relation to the therapeutic and prophylactic aspects of the invention, it will be appreciated by persons skilled in the art that binding of the agent to IL1RAP present on the surface of the pathological stem cells and/or progenitor cells may lead to a modulation (i.e. an increase or decrease) of a biological activity of IL1RAP. However, such a modulatory effect is not essential; for example, the agents of the invention may elicit a therapeutic and prophylactic effect simply by virtue of binding to IL1RAP on the surface of the pathological stem cells and/or progenitor cells, which in turn may trigger the immune system to induce cell death (e.g. by ADCC).

By "biological activity of IL1RAP" we include any interaction or signalling event which involves IL1RAP on pathological stem cells and/or progenitor cells. For example, in one embodiment the agent is capable of blocking binding of one or more co-receptors to IL1RAP (such as IL1R1, ST2, C-KIT and/or IL1RL2).

Such inhibition of the biological activity of IL1RAP by an agent of the invention may be in whole or in part. For example, the agent may inhibit the biological activity of IL1RAP by at least 10%, preferably at least 20%, 30%, 40%, 50%, 60%, 70%, 80% or 90%, and most preferably by 100% compared to the biological activity of IL1RAP in pathological stem cells and/or progenitor cells which have not been exposed to the agent. In a preferred embodiment, the agent is capable of inhibiting the biological activity of IL1RAP by 50% or more compared to the biological activity of IL1RAP in pathological stem cells and/or progenitor cells which have not been exposed to the agent.

Likewise, it will be appreciated that inhibition of growth and/or proliferation of the pathological stem cells and/or progenitor cells may be in whole or in part. For example, the agent may inhibit the growth and/or proliferation of the pathological stem cells and/or progenitor cells by at least 10%, preferably at least 20%, 30%, 40%, 50%, 60%, 70%, 80% or 90%, and most preferably by 100% compared to the growth and/or proliferation of the pathological stem cells and/or progenitor cells which have not been exposed to the agent.

Similarly, it will be appreciated that the induction of differentiation of pathological stem cells and/or progenitor cells may be to any extent. For example, the agent may induce differentiation of the pathological stem cells and/or progenitor cells by at least 10%, preferably at least 20%, 30%, 40%, 50%, 60%, 70%, 80% or 90%, and most preferably by 100% compared to the differentiation of the pathological stem cells and/or progenitor cells which have not been exposed to the agent.

In a further preferred embodiment, the agent is capable of killing the pathological stem cells and/or progenitor cells. In particular, the agent may be capable of inducing stem cell and/or progenitor cell death by apoptosis or autophagy. For example, the agent may induce apoptosis by antibody-dependent cell-mediated cytotoxicity (ADCC).

As indicated above, the agents of the invention may comprise or consist of any suitable chemical entity constituting a binding moiety with specificity for IL1RAP.

Methods for detecting interactions between a test chemical entity and IL1RAP are well known in the art. For example ultrafiltration with ion spray mass spectroscopy/HPLC methods or other physical and analytical methods may be used. In addition, Fluorescence Energy Resonance Transfer (FRET) methods may be used, in which binding of two fluorescent labelled entities may be measured by measuring the interaction of the fluorescent labels when in close proximity to each other.

Alternative methods of detecting binding of IL1RAP to macromolecules, for example DNA, RNA, proteins and phospholipids, include a surface plasmon resonance assay, for example as described in Plant et al., 1995, *Analyt Biochem* 226(2), 342-348. Such methods may make use of a polypeptide that is labelled, for example with a radioactive or fluorescent label.

A further method of identifying a chemical entity that is capable of binding to IL1RAP is one where the protein is exposed to the compound and any binding of the compound to the said protein is detected and/or measured. The binding constant for the binding of the compound to the polypeptide may be determined. Suitable methods for detecting and/or measuring (quantifying) the binding of a compound to a polypeptide are well known to those skilled in the art and may be performed, for example, using a method capable of high throughput operation, for example a chip-based method. New technology, called VLSIPS™, has enabled the production of extremely small chips that contain hundreds of thousands or more of different molecular probes. These biological chips have probes arranged in arrays, each probe assigned a specific location. Biological chips have been produced in which each location has a scale of, for example, ten microns. The chips can be used to determine whether target molecules interact with any of the probes on the chip. After exposing the array to target molecules under selected test conditions, scanning devices can examine each location in the array and determine whether a target molecule has interacted with the probe at that location.

Another method of identifying compounds with binding affinity for IL1RAP is the yeast two-hybrid system, where the polypeptides of the invention can be used to "capture" proteins that bind IL1RAP. The yeast two-hybrid system is described in Fields & Song, Nature 340:245-246 (1989).

In one preferred embodiment, the agent comprises or consists of a polypeptide.

For example, the agent may comprise or consist of an antibody or an antigen-binding fragment thereof with binding specificity for IL1RAP, or a variant, fusion or derivative of said antibody or antigen-binding fragment, or a fusion of a said variant or derivative thereof, which retains the binding specificity for IL1RAP.

By "antibody" we include substantially intact antibody molecules, as well as chimaeric antibodies, humanised antibodies, human antibodies (wherein at least one amino acid is mutated relative to the naturally occurring human antibodies), single chain antibodies, bispecific antibodies, antibody heavy chains, antibody light chains, homodimers and heterodimers of antibody heavy and/or light chains, and antigen binding fragments and derivatives of the same.

By "antigen-binding fragment" we mean a functional fragment of an antibody that is capable of binding to IL1RAP.

Preferably, the antigen-binding fragment is selected from the group consisting of Fv fragments (e.g. single chain Fv and disulphide-bonded Fv), Fab-like fragments (e.g. Fab fragments, Fab' fragments and F(ab)$_2$ fragments), single variable domains (e.g. $V_H$ and $V_L$ domains) and domain antibodies (dAbs, including single and dual formats [i.e. dAb-linker-dAb]).

The advantages of using antibody fragments, rather than whole antibodies, are several-fold. The smaller size of the fragments may lead to improved pharmacological properties, such as better penetration of solid tissue. Moreover, antigen-binding fragments such as Fab, Fv, ScFv and dAb antibody fragments can be expressed in and secreted from *E. coli*, thus allowing the facile production of large amounts of the said fragments.

Also included within the scope of the invention are modified versions of antibodies and antigen-binding fragments thereof, e.g. modified by the covalent attachment of polyethylene glycol or other suitable polymer (see below).

Methods of generating antibodies and antibody fragments are well known in the art. For example, antibodies may be generated via any one of several methods which employ induction of in vivo production of antibody molecules, screening of immunoglobulin libraries (Orlandi. et al, 1989. *Proc. Natl. Acad. Sci. U.S.A.* 86:3833-3837; Winter et al., 1991, *Nature* 349:293-299) or generation of monoclonal antibody molecules by cell lines in culture. These include, but are not limited to, the hybridoma technique, the human B-cell hybridoma technique, and the Epstein-Barr virus (EBV)-hybridoma technique (Kohler et al., 1975. *Nature* 256:4950497; Kozbor et al., 1985. *J. Immunol. Methods* 81:31-42; Cote et al., 1983. *Proc. Natl. Acad. Sci. USA* 80:2026-2030; Cole et al., 1984. *Mol. Cell. Biol.* 62:109-120).

Suitable monoclonal antibodies to selected antigens may be prepared by known techniques, for example those disclosed in "*Monoclonal Antibodies: A manual of techniques*", H Zola (CRC Press, 1988) and in "*Monoclonal Hybridoma Antibodies: Techniques and Applications*", J G R Hurrell (CRC Press, 1982).

Likewise, antibody fragments can be obtained using methods well known in the art (see, for example, Harlow & Lane, 1988, "*Antibodies: A Laboratory Manual*", Cold Spring Harbor Laboratory, New York). For example, antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment. Alternatively, antibody fragments can be obtained by pepsin or papain digestion of whole antibodies by conventional methods.

It will be appreciated by persons skilled in the art that for human therapy or diagnostics, human or humanised antibodies are preferably used. Humanised forms of non-human (e.g. murine) antibodies are genetically engineered chimaeric antibodies or antibody fragments having preferably minimal-portions derived from non-human antibodies. Humanised antibodies include antibodies in which complementary determining regions of a human antibody (recipient antibody) are replaced by residues from a complementary determining region of a non human species (donor antibody) such as mouse, rat of rabbit having the desired functionality. In some instances, Fv framework residues of the human antibody are replaced by corresponding non-human residues. Humanised antibodies may also comprise residues which are found neither in the recipient antibody nor in the imported complementarity determining region or framework sequences. In general, the humanised antibody will comprise substantially all of at least one, and typically two, variable domains, in which all or substantially all of the complementarity determining regions correspond to those of a non human antibody and all, or substantially all, of the framework regions correspond to those of a relevant human consensus sequence. Humanised antibodies optimally also include at least a portion of an antibody constant region, such as an Fc region, typically derived from a human antibody (see, for example, Jones et al., 1986. *Nature* 321:522-525; Riechmann et al., 1988, *Nature* 332:323-329; Presta, 1992, *Curr. Op. Struct. Biol.* 2:593-596).

Methods for humanising non-human antibodies are well known in the art. Generally, the humanised antibody has one or more amino acid residues introduced into it from a source which is non-human. These non-human amino acid residues, often referred to as imported residues, are typically taken from an imported variable domain. Humanisation can be essentially performed as described (see, for example, Jones et al., 1986, *Nature* 321:522-525; Reichmann et al., 1988. *Nature* 332:323-327; Verhoeyen et al., 1988, *Science* 239: 1534-15361; U.S. Pat. No. 4,816,567) by substituting human complementarity determining regions with corresponding rodent complementarity determining regions. Accordingly, such humanised antibodies are chimaeric antibodies, wherein substantially less than an intact human variable domain has been substituted by the corresponding sequence from a non-human species. In practice, humanised antibodies may be typically human antibodies in which some complementarity determining region residues and possibly some framework residues are substituted by residues from analogous sites in rodent antibodies.

Human antibodies can also be identified using various techniques known in the art, including phage display libraries (see, for example, Hoogenboom & Wnter, 1991, *J. Mol. Biol.* 227:381; Marks et al., 1991, *J. Mol. Biol.* 222:581; Cole et al., 1985, In: *Monoclonal antibodies and Cancer Therapy*, Alan R. Liss, pp. 77; Boerner et al., 1991. *J. Immunol.* 147:86-95).

Once suitable antibodies are obtained, they may be tested for activity, for example by ELISA.

In an alternative embodiment of the first aspect of the invention, the agent comprises or consists of a non-immunoglobulin binding moiety, for example as described in Skerra, *Curr Opin Biotechnol.* 2007 August; 18(4):295-304.

In a further alternative embodiment, the agent comprises or consists of an aptamer. For example, the agent may comprise or consist of a peptide aptamer or a nucleic acid aptamer (see Hoppe-Seyler & Butz, 2000, *J Mol Med.* 78 (8): 426-30; Bunka D H & Stockley P G, 2006, *Nat Rev Microbiol.* 4 (8): 588-96 and Drabovich et al., 2006, *Anal Chem.* 78 (9): 3171-8).

In a still further alternative embodiment, the agent comprises or consists of a small chemical entity. Such entities with IL1RAP binding properties may be identified by screening commercial libraries of small compounds (for example, as available from ChemBridge Corporation, San Diego, USA)

In addition to the binding moiety, the agents of the invention may further comprise a moiety for increasing the in vivo half-life of the agent, such as but not limited to polyethylene glycol (PEG), human serum albumin, glycosylation groups, fatty acids and dextran. Such further moieties may be conjugated or otherwise combined with the binding moiety using methods well known in the art.

Likewise, it will be appreciated that the agents of the invention may further comprise a cytotoxic moiety.

For example, the cytotoxic moiety may comprise or consist of a radioisotope, such as astatine-211, bismuth-212, bismuth-213, iodine-131, yttrium-90, lutetium-177, samarium-153 and palladium-109.

Alternatively, the cytotoxic moiety may comprise or consist of a toxin (such as saporin or calicheamicin).

In a further alternative, the cytotoxic moiety may comprise or consist of a chemotherapeutic agent (such as an antimetabolite).

Likewise, it will be appreciated that the agents of the invention may further comprise a detectable moiety.

For example, the detectable moiety may comprise or consist of a radioisotope., such as technitium-99m, indium-111, gallium-67, gallium-68, arsenic-72, zirconium-89, iodine-12 or thallium-201.

Alternatively, the detectable moiety comprises or consists of a paramagnetic isotope, such as gadolinium-157, manganese-55, dysprosium-162, chromium-52 or iron-56.

Cytotoxic and detectable moieties may be conjugated or otherwise combined with the binding moiety using methods well known in the art (for example, the existing immuno-conjugate therapy, gemtuzumab ozogamicin [tradename: Mylotarg®], comprises a monoclonal antibody linked to the cytotoxin calicheamicin).

A third aspect of the invention provides a pharmaceutical composition comprising an effective amount of an agent as defined in relation to the first or second aspects of the invention together with a pharmaceutical acceptable buffer, diluent, carrier, adjuvant or excipient.

Additional compounds may also be included in the compositions, including, chelating agents such as EDTA, citrate, EGTA or glutathione.

The pharmaceutical compositions may be prepared in a manner known in the art that is sufficiently storage stable and suitable for administration to humans and animals. For example, the pharmaceutical compositions may be lyophilised, e.g. through freeze drying, spray drying, spray cooling, or through use of particle formation from supercritical particle formation.

By "pharmaceutically acceptable" we mean a non-toxic material that does not decrease the effectiveness of the IL1RAP-binding activity of the agent of the invention. Such pharmaceutically acceptable buffers, carriers or excipients are well-known in the art (see Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000), he disclosures of which are incorporated herein by reference).

The term "buffer" is intended to mean an aqueous solution containing an acid-base mixture with the purpose of stabilising pH. Examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES.

The term "diluent" is intended to mean an aqueous or non-aqueous solution with the purpose of diluting the agent in the pharmaceutical preparation. The diluent may be one or more of saline, water, polyethylene glycol, propylene glycol, ethanol or oils (such as safflower oil, corn oil, peanut oil, cottonseed oil or sesame oil).

The term "adjuvant" is intended to mean any compound added to the formulation to increase the biological effect of the agent of the invention. The adjuvant may be one or more of zinc, copper or silver salts with different anions, for example, but not limited to fluoride, chloride, bromide, iodide, tiocyanate, sulfite, hydroxide, phosphate, carbonate, lactate, glycolate, citrate, borate, tartrate, and acetates of different acyl composition. The adjuvant may also be cationic polymers such as cationic cellulose ethers, cationic cellulose esters, deacetylated hyaluronic acid, chitosan, cationic dendrimers, cationic synthetic polymers such as poly (vinyl imidazole), and cationic polypeptides such as polyhistidine, polylysine, polyarginine, and peptides containing these amino acids.

The excipient may be one or more of carbohydrates, polymers, lipids and minerals. Examples of carbohydrates include lactose, glucose, sucrose, mannitol, and cyclodextrines, which are added to the composition, e.g., for facilitating lyophilisation. Examples of polymers are starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone, all of different molecular weight, which are added to the composition, e.g., for viscosity control, for achieving bioadhesion, or for protecting the lipid from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

The agents of the invention may be formulated into any type of pharmaceutical composition known in the art to be suitable for the delivery thereof.

In one embodiment, the pharmaceutical compositions of the invention may be in the form of a liposome, in which the agent is combined, in addition to other pharmaceutically acceptable carriers, with amphipathic agents such as lipids, which exist in aggregated forms as micelles, insoluble monolayers and liquid crystals. Suitable lipids for liposomal formulation include, without limitation, monoglycerides, diglycerides, sulfatides, lysolecithin, phospholipids, saponin, bile acids, and the like. Suitable lipids also include the lipids above modified by poly(ethylene glycol) in the polar headgroup for prolonging bloodstream circulation time. Preparation of such liposomal formulations is can be found in for example U.S. Pat. No. 4,235,871, the disclosures of which are incorporated herein by reference.

The pharmaceutical compositions of the invention may also be in the form of biodegradable microspheres. Aliphatic polyesters, such as poly(lactic acid) (PLA), poly(glycolic acid) (PGA), copolymers of PLA and PGA (PLGA) or poly(carprolactone) (PCL), and polyanhydrides have been widely used as biodegradable polymers in the production of microspheres. Preparations of such microspheres can be found in U.S. Pat. No. 5,851,451 and in EP 0 213 303, the disclosures of which are incorporated herein by reference.

In a further embodiment, the pharmaceutical compositions of the invention are provided in the form of polymer gels, where polymers such as starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polyvinyl imidazole, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone are used for thickening of the solution containing the agent. The polymers may also comprise gelatin or collagen.

Alternatively, the agents may simply be dissolved in saline, water, polyethylene glycol, propylene glycol, ethanol or oils (such as safflower oil, corn oil, peanut oil, cottonseed oil or sesame oil), tragacanth gum, and/or various buffers.

It will be appreciated that the pharmaceutical compositions of the invention may include ions and a defined pH for potentiation of action of the active agent. Additionally, the compositions may be subjected to conventional pharmaceutical operations such as sterilisation and/or may contain conventional adjuvants such as preservatives, stabilisers, wetting agents, emulsifiers, buffers, fillers, etc.

The pharmaceutical compositions according to the invention may be administered via any suitable route known to those skilled in the art. Thus, possible routes of administration include parenteral (intravenous, subcutaneous, and intramuscular), topical, ocular, nasal, pulmonar, buccal, oral, parenteral, vaginal and rectal. Also administration from implants is possible.

In one preferred embodiment, the pharmaceutical compositions are administered parenterally, for example, intravenously, intracerebroventricularly, intraarticularly, intraarterially, intraperitoneally, intrathecally, intraventricularly, intrasternally, intracranially, intramuscularly or subcutaneously, or they may be administered by infusion techniques. They are conveniently used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Thus, the pharmaceutical compositions of the invention are particularly suitable for parenteral, e.g. intravenous, administration.

Alternatively, the pharmaceutical compositions may be administered intranasally or by inhalation (for example, in the form of an aerosol spray presentation from a pressurised container, pump, spray or nebuliser with the use of a suitable propellant, such as dichlorodifluoromethane, trichlorofluoro-methane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas). In the case of a pressurised aerosol, the dosage unit may be determined by providing a valve to deliver a metered amount. The pressurised container, pump, spray or nebuliser may contain a solution or suspension of the active polypeptide, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

The pharmaceutical compositions will be administered to a patient in a pharmaceutically effective dose. A 'therapeutically effective amount', or 'effective amount', or 'therapeutically effective', as used herein, refers to that amount which provides a therapeutic effect for a given condition and administration regimen. This is a predetermined quantity of active material calculated to produce a desired therapeutic effect in association with the required additive and diluent, i.e. a carrier or administration vehicle. Further, it is intended to mean an amount sufficient to reduce and most preferably prevent, a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art. The administration of the pharmaceutically effective dose can be carried out both by single administration in the form of an individual dose unit or else several smaller dose units and also by multiple administrations of subdivided doses at specific intervals. Alternatively, the does may be provided as a continuous infusion over a prolonged period.

The polypeptides can be formulated at various concentrations, depending on the efficacy/toxicity of the compound being used. Preferably, the formulation comprises the active agent at a concentration of between 0.1 µM and 1 mM, more preferably between 1 µM and 500 µM, between 500 µM and 1 mM, between 300 µM and 700 µM, between 1 µM and 100 µM, between 100 µM and 200 µM, between 200 µM and 300 µM, between 300 µM and 400 µM, between 400 µM and 500 µM and most preferably about 500 µM.

It will be appreciated by persons skilled in the art that the pharmaceutical compositions of the invention may be administered alone or in combination with other therapeutic agents used in the treatment of a neoplastic hematologic disorder, such as inhibitors of tyrosine kinase (e.g. imatinib mesylate [Glivec®], dasatinib, nilotinib), omacetaxine, antimetabolites (e.g. cytarabine, hydroxyurea), alkylating agents, Interferon alpha-2b and/or steroids.

A fourth aspect of the invention provides a kit comprising an agent as defined in relation to the first or second aspects of the invention or a pharmaceutical composition according to the third aspect of the invention.

A fifth aspect of the invention provides the use of an agent as defined in relation to the first or second aspects of the invention in the preparation of a medicament for inducing cell death and/or inhibiting the growth and/or proliferation of pathological stem cells and/or progenitor cells associated with a neoplastic hematologic disorder, wherein the stem cells and/or progenitor cells express IL1RAP.

The agent may also be for use in inducing differentiation of pathological stem and/or progenitor cells which express IL1RAP.

A related sixth aspect of the invention provides the use of an agent as defined in relation to the first or second aspects of the invention in the preparation of a diagnostic agent for detecting pathological stem cells and/or progenitor cells associated with a neoplastic hematologic disorder, wherein the stem cells and/or progenitor cells express IL1RAP.

A related seventh aspect of the invention provides the use of an agent as defined in relation to the first or second aspects of the invention for detecting pathological stem cells and/or progenitor cells associated with a neoplastic hematologic disorder, wherein the stem cells and/or progenitor cells express IL1RAP.

In one embodiment of the above use aspects of the invention, the neoplastic hematologic disorder is a leukemia.

In a further embodiment, the neoplastic hematologic disorder may be associated with cells comprising a BCR/ABL1 fusion gene. For example, the pathological stem cells and/or progenitor cells may comprise a BCR/ABL1 fusion gene.

In a related embodiment, the neoplastic hematologic disorder may be associated with cells comprising a Ph chromosome. For example, the pathological stem cells and/or progenitor cells comprise a Ph chromosome. By "Ph chromosome" in this context we mean a specific chromosomal abnormality resulting from a reciprocal translocation between chromosome 9 and 22, specifically designated t(9;22)(q34;q11). An example of a neoplastic hematologic disorder associated with cells comprising a Ph chromosome is chronic myeloid (or myelogenous) leukemia (CML).

However, it will be appreciated by persons skilled in the art that the agents of the invention may also be used in the treatment and/or diagnosis of neoplastic hematologic disorders which are not associated with cells comprising a Philadelphia (Ph) chromosome (but nevertheless show upregulation of IL1RAP). Such neoplastic hematologic disorders which are associated with cells which do not comprise a Ph chromosome include the myelodysplastic syndromes (MDS) and myeloproliferative disorders (MPD) such as polycythemia vera (PV), essential thrombocytosis (ET) and myelofibrosis (MF).

More specifically, the neoplastic hematologic disorder may be selected from the group consisting of chronic myeloid leukemia (CML), myeloproliferative disorders (MPD), myelodysplastic syndrome (MDS), acute lymphoblastic leukemia (ALL) and acute myeloid leukemia (AML).

In one particularly preferred embodiment, the neoplastic hematologic disorder is chronic myeloid leukemia (CML).

A eighth aspect of the invention provides a method for inducing cell death and/or inhibiting the growth and/or proliferation of pathological stem cells and/or progenitor cells associated with a neoplastic hematologic disorder in an individual, comprising the step of administering to the individual an effective amount of an agent as defined in relation to the first or second aspects of the invention, or a pharmaceutical composition according to the third aspect of the invention, wherein the stem cells and/or progenitor cells express IL1RAP.

The method may also be for inducing differentiation of pathological stem and/or progenitor cells which express IL1RAP.

Thus the invention provides methods for the treatment of neoplastic hematologic disorders. By 'treatment' we include both therapeutic and prophylactic treatment of the patient. The term 'prophylactic' is used to encompass the use of a polypeptide or formulation described herein which either prevents or reduces the likelihood of a neoplastic hematologic disorder in a patient or subject.

A ninth aspect of the invention provides a method for detecting pathological stem cells and/or progenitor cells associated with neoplastic hematologic disorder in an individual, comprising the step of administering to the individual an effective amount of an agent as defined in relation to the first or second aspects of the invention, or a pharmaceutical composition according to the third aspect of the invention, wherein the stem cells and/or progenitor cells express IL1RAP.

A tenth aspect of the invention provides an in vitro method for diagnosing or prognosing a neoplastic hematologic disorder, the method comprising:
  (a) providing a bone marrow or peripheral blood sample of haematopoietic cells from an individual to be tested;
  (b) isolating a subpopulation of $CD34^+$, $CD38^-$ cells from the haematopoietic cells; and (c) determining whether stem cells, contained within the CD34+, CD38− cells, express the cell surface markers IL1RAP.

wherein stem cells that exhibit the cell surface marker profile CD34+, CD38− and IL1RAP+ exhibit are indicative of the individual having or developing leukemia.

In one embodiment of the above method aspects of the invention, the neoplastic hematologic disorder is a leukemia.

In a further embodiment, the neoplastic hematologic disorder may be associated with cells comprising a BCR/ABL1 fusion gene. For example, the pathological stem cells may comprise a BCR/ABL1 fusion gene.

In a related embodiment, the neoplastic hematologic disorder may be associated with cells comprising a Ph chromosome. For example, the pathological stem cells comprise a Ph chromosome. By "Ph chromosome" in this context we mean a specific chromosomal abnormality resulting from a reciprocal translocation between chromosome 9 and 22, specifically designated t(9;22)(q34;q11). An example of a neoplastic hematologic disorder associated with cells comprising a Ph chromosome is chronic myeloid (or myelogenous) leukemia (CML).

However, it will be appreciated by persons skilled in the art that the agents of the invention may also be used in the treatment and/or diagnosis of neoplastic hematologic disorders which are not associated with cells comprising a Philadelphia (Ph) chromosome (but nevertheless show upregulation of IL1RAP). Such neoplastic hematologic disorders which are associated with cells which do not comprise a Ph chromosome include the myelodysplastic syndromes (MDS) and myeloproliferative disorders (MPD) such as polycythemia vera (PV), essential thrombocytosis (ET) and myelofibrosis (MF).

More specifically, the neoplastic hematologic disorder may be selected from the group consisting of chronic myeloid leukemia (CML), myeloproliferative disorders (MPD), myelodysplastic syndrome (MDS), acute lymphoblastic leukemia (ALL) and acute myeloid leukemia (AML).

In one particularly preferred embodiment, the neoplastic hematologic disorder is chronic myeloid leukemia (CML).

Preferred, non-limiting examples which embody certain aspects of the invention will now be described, with reference to the following figures:

FIG. 1. P210 BCR/ABL1 Expression Induces IL1RAP Expression in Cord Blood CD34+ Cells Flow cytometric analysis confirms that IL1RAP expression is induced upon retroviral P210 BCR/ABL1 expression in cord blood CD34+ cells, three days post transduction. CD34+GFP+ cells were gated according to the gates in the dot plots. The histogram shows the expression of IL1RAP for negative control staining (white), MIG control (light gray) and MIG-P210 (dark gray). The numbers in the dot plots show the percentage of cells within individual gates/quadrants. A representative experiment out of three is shown.

Figure 2B:
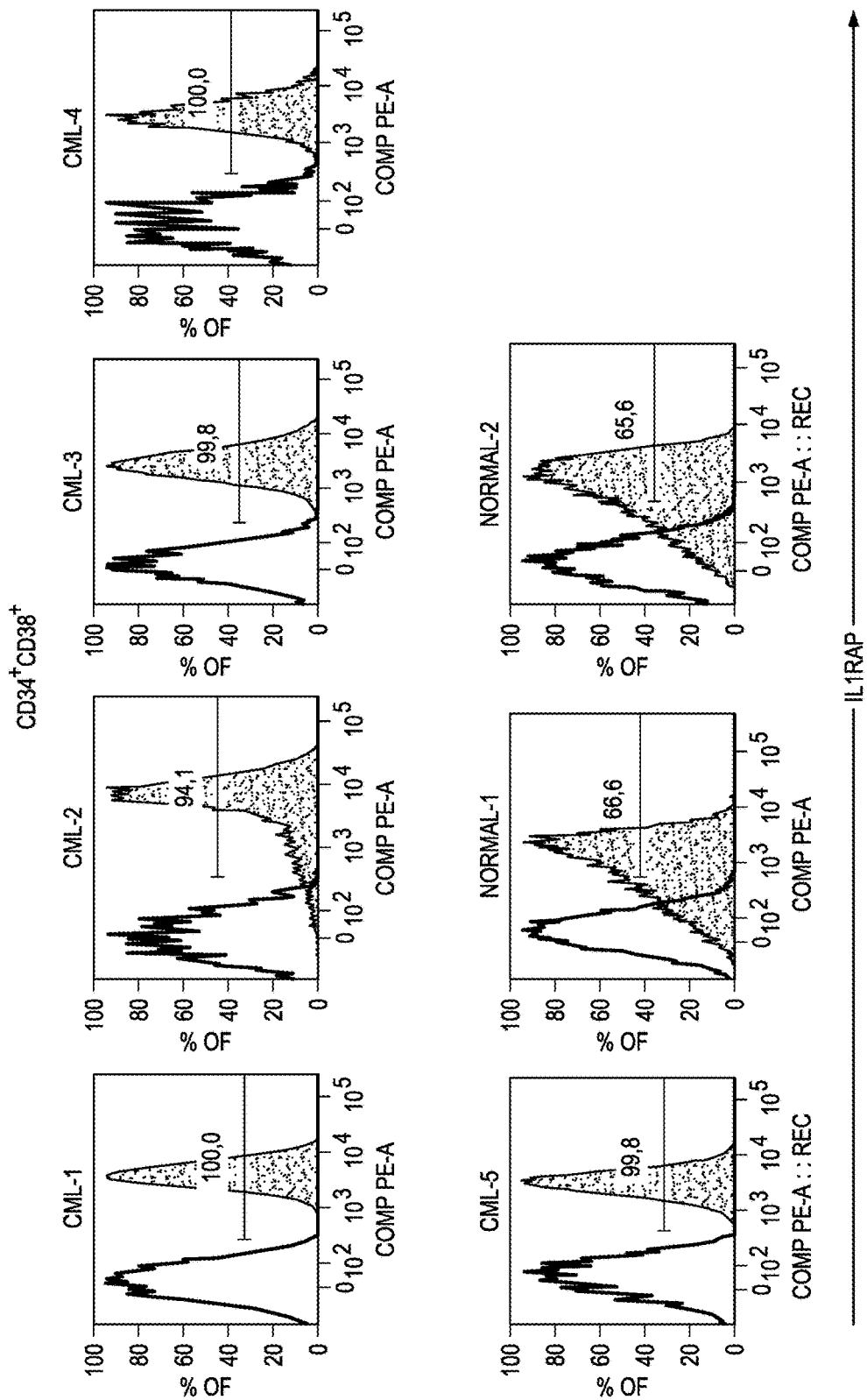
Figure 2C:
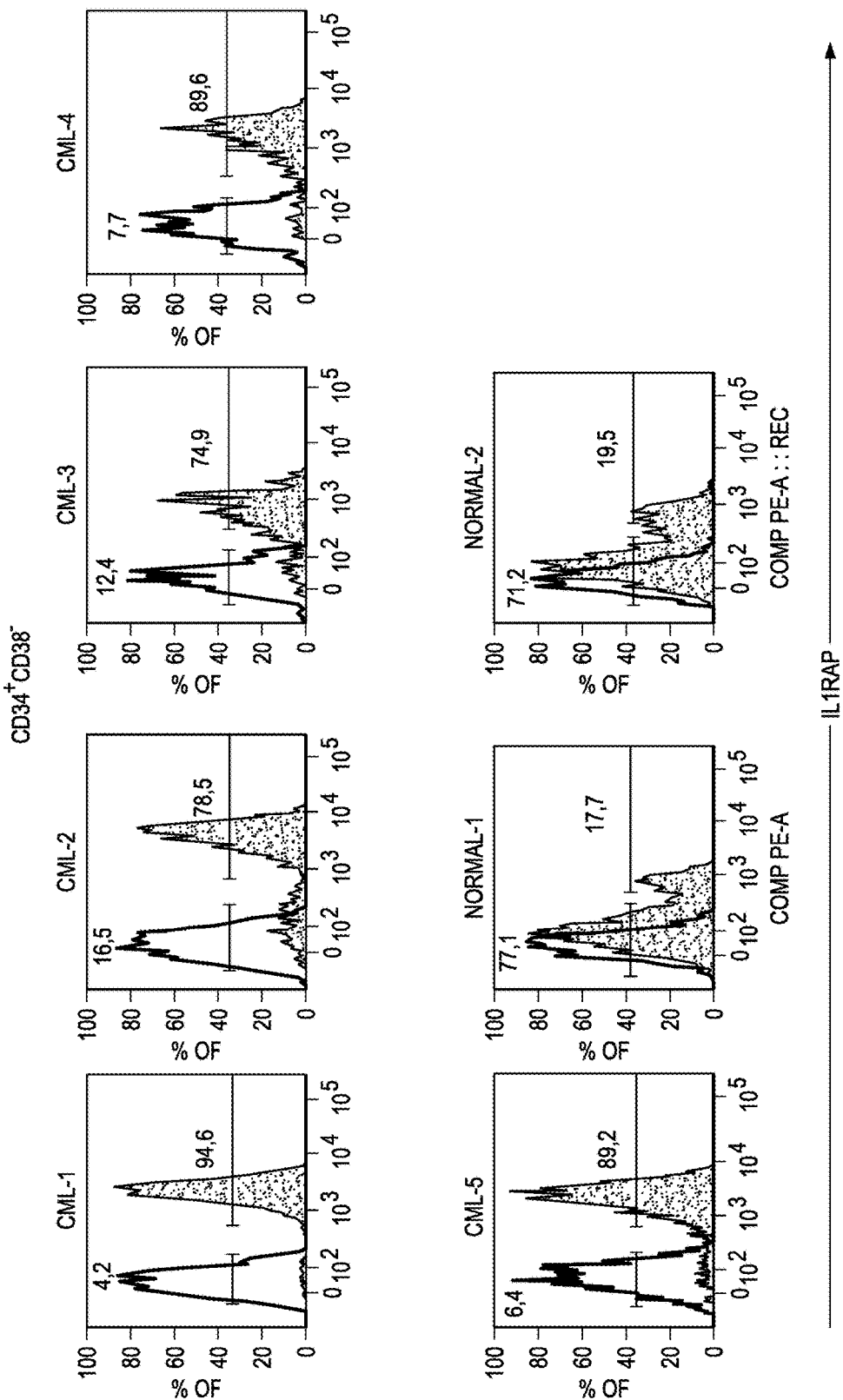

FIGS. 2A-C. IL1RAP is Upregulated in Primitive CML Cells

In FIG. 2A, FACS analysis on CD34+ cells from five CML patients and from 2 normal bm samples. FACS dot plot showing gating for CD34+CD38+ or CD34+CD38− cells in a representative CML patient.

FIG. 2B shows histograms of IL1RAP expression within CD34+CD38+ cells.

FIG. 2C shows histograms of IL1RAP expression within CD34+CD38− cells. White represent control stained samples and gray represent IL1RAP stained samples. The sorting gates for CD34+CD38−IL1RAP− and CD34+CD38−IL1RAP+ cells are outlined in the histograms. The numbers in the dot plot and histograms show the percentage of cells within individual gates/quadrants.

Figure 3:
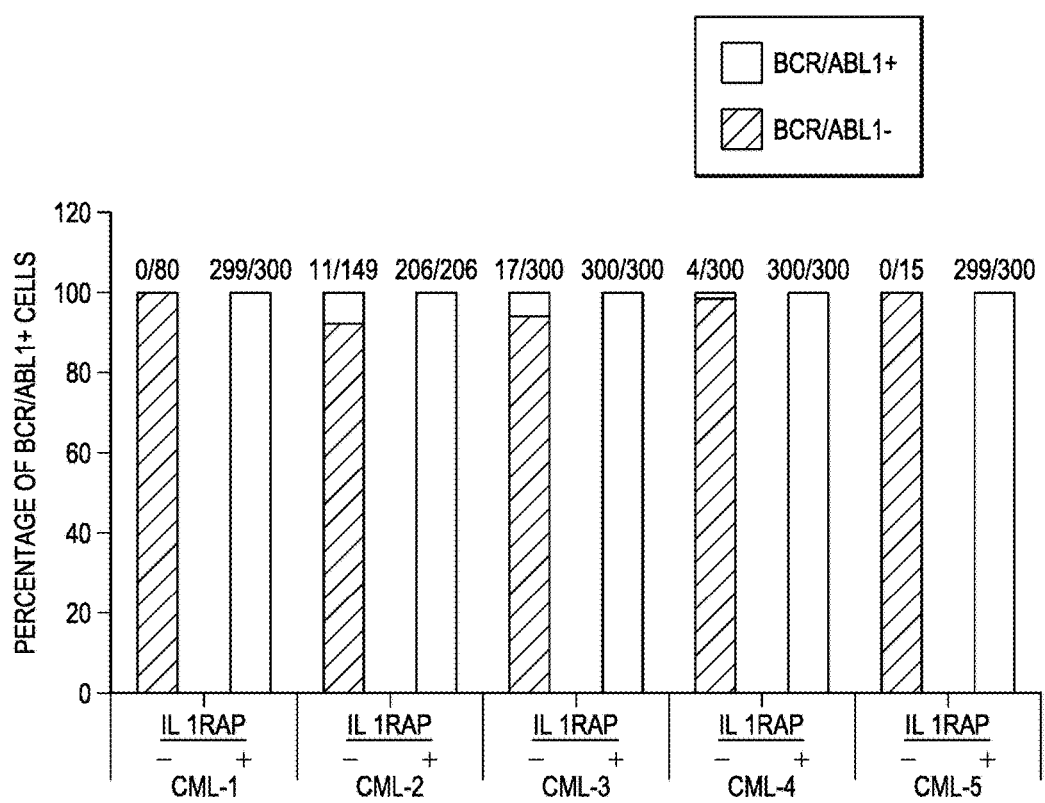

FIG. 3. IL1RAP Expression Distinguishes Ph+ from Ph− CML Cells within the CD34+CD38− Cell Compartment Flow-drop-FISH on CML CD34+CD38−IL1RAP− and CD34+CD38−IL1RAP+ cells from 5 CML patient samples revealed an almost complete separation between BCR/ABL1− and BCR/ABL1+ cells, respectively. Black bars represent BCR/ABL1 negative cells and white bars represent BCR/ABL1 positive cells. Outlined at the top of each bar is the number of Ph+ cells of the total nuclei scored.

Figure 4A:
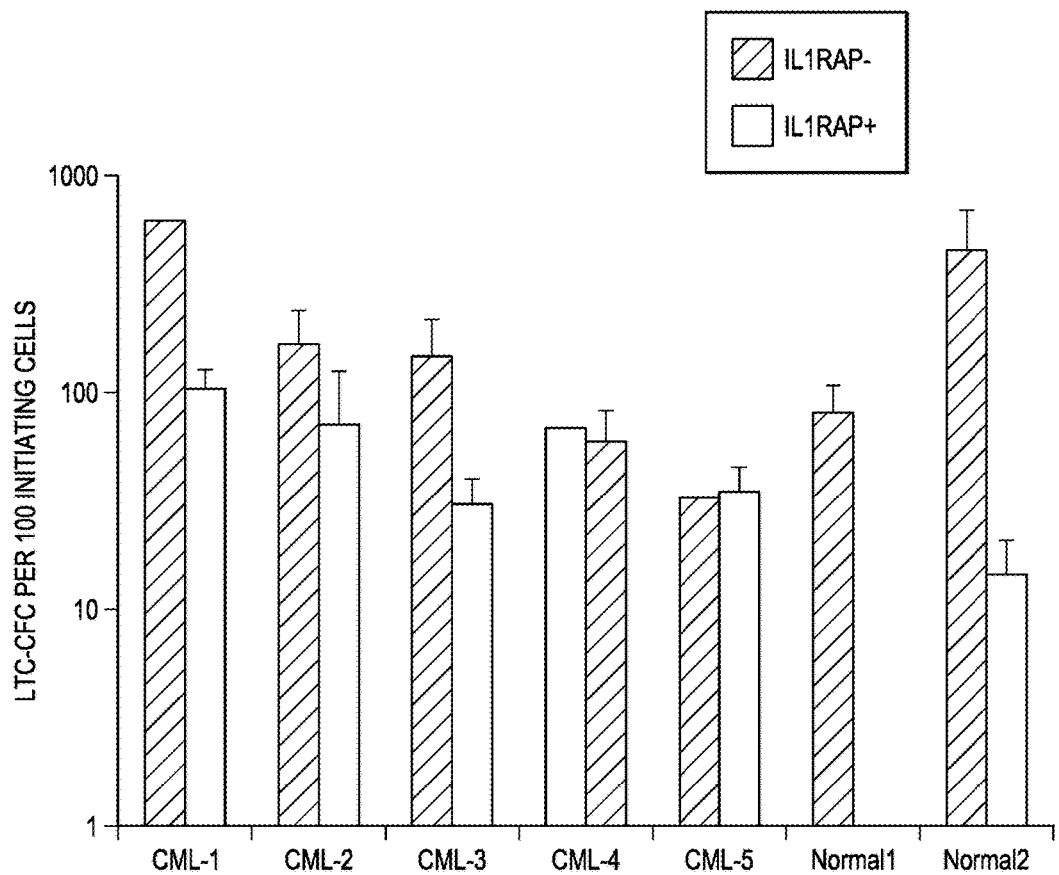
Figure 4B:
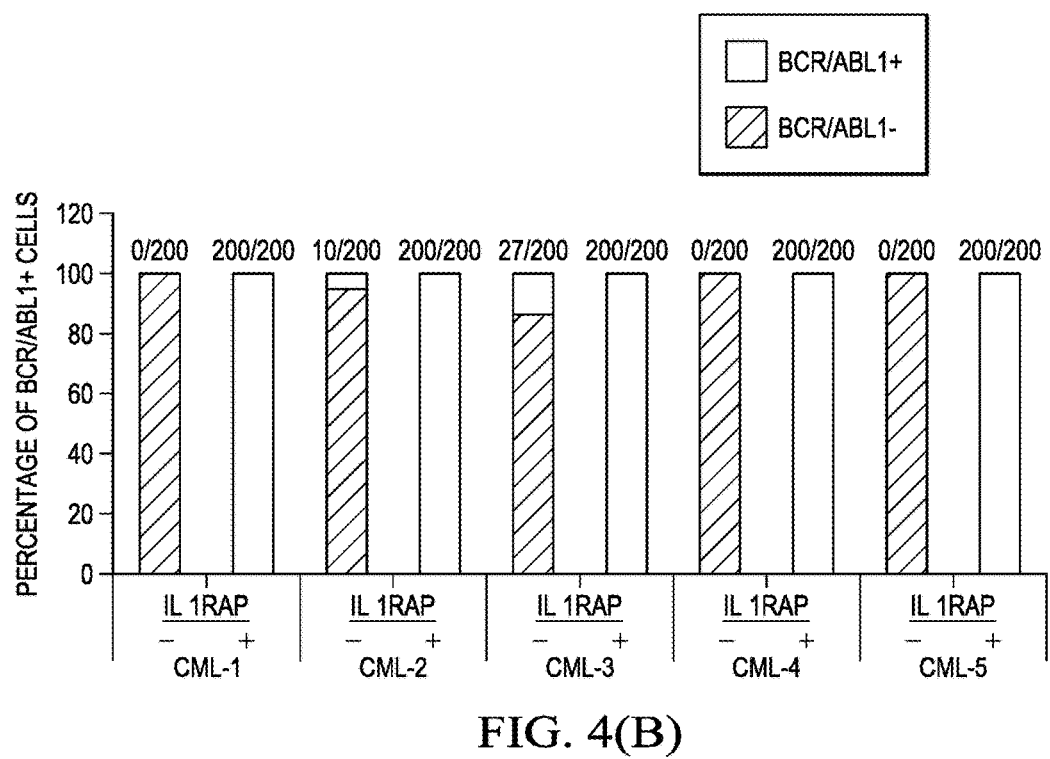

FIGS. 4A-B. IL1RAP Expression Distinguishes Ph+ CML Stem Cells from Normal HSC

FIG. 4A shows the number of LTC-CFC derived from CD34+CD38−IL1RAP− and CD34+CD38−IL1RAP+ cells. Black bars represent IL1RAP− cells and white bars represent IL1RAP+ cells. Interphase FISH on LTC-CFC.

In FIG. 4B black bars represent BCR/ABL1 negative cells and white bars represent BCR/ABL1 positive cells. Outlined at the top of each bar is the number of Ph+ cells of the total nuclei scored.

Figure 5A:
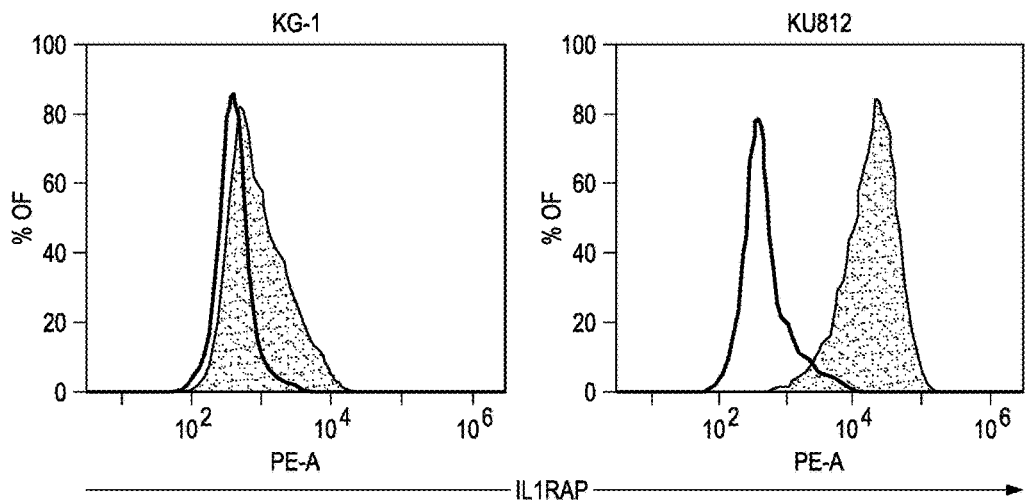
Figure 5B:
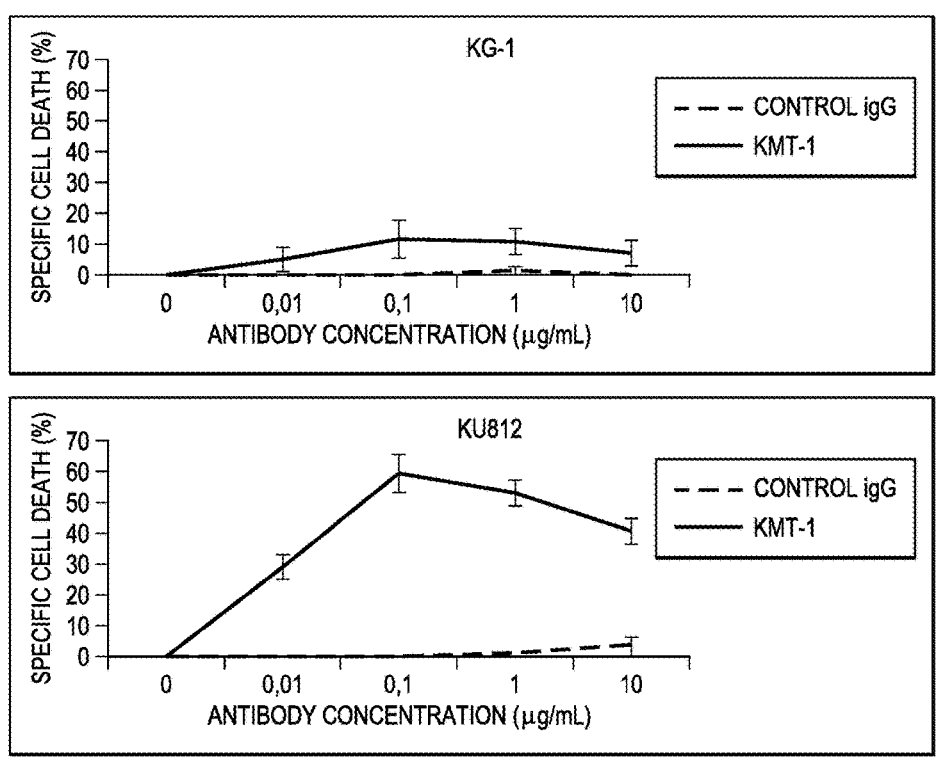

FIGS. 5A-B.—Killing of a CML Cell Line by Antibody Targeting of IL1RAP

FIG. 5A shows histograms of IL1RAP expression on KU812 cells derived from a CML patient and containing a Philadelphia chromosome, compared to expression on KG-1 cells lacking a Philadelphia chromosome. White show control stained samples and gray show KMT-1 stained samples.

FIG. 5B shows the leukemic cell line KG-1 was devoid of IL1RAP expression, whereas KU812 express IL1RAP. As a consequence, low level of antibody induced cell death was observed in KG-1, while a dose-dependent ADCC effect was observed using KMT-1 on KU812 cells. As a control for unspecific ADCC effects, a rabbit IgG antibody was also used in the experiments. The graph shows the average and standard deviation of antibody induced cell death from three independent experiments.

Figure 6A:
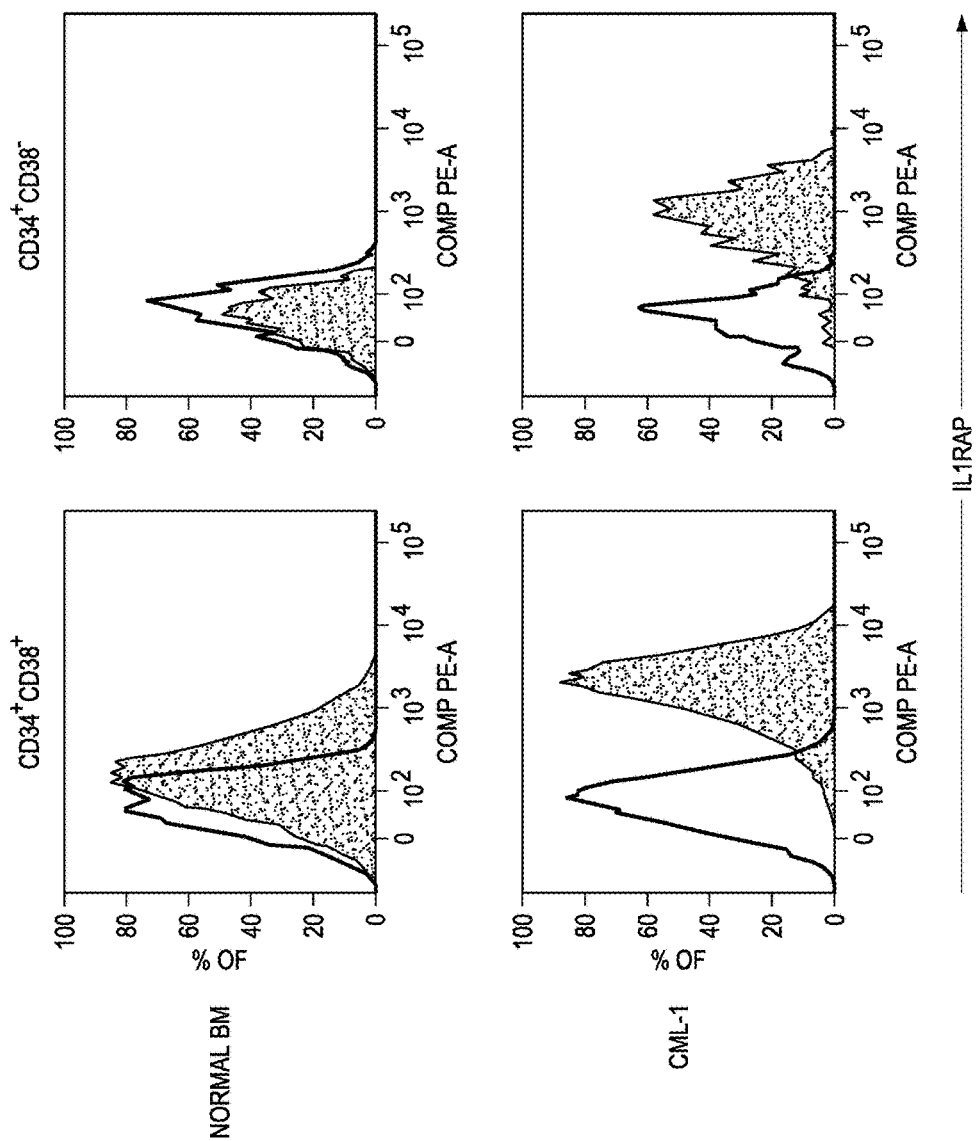
Figure 6B:
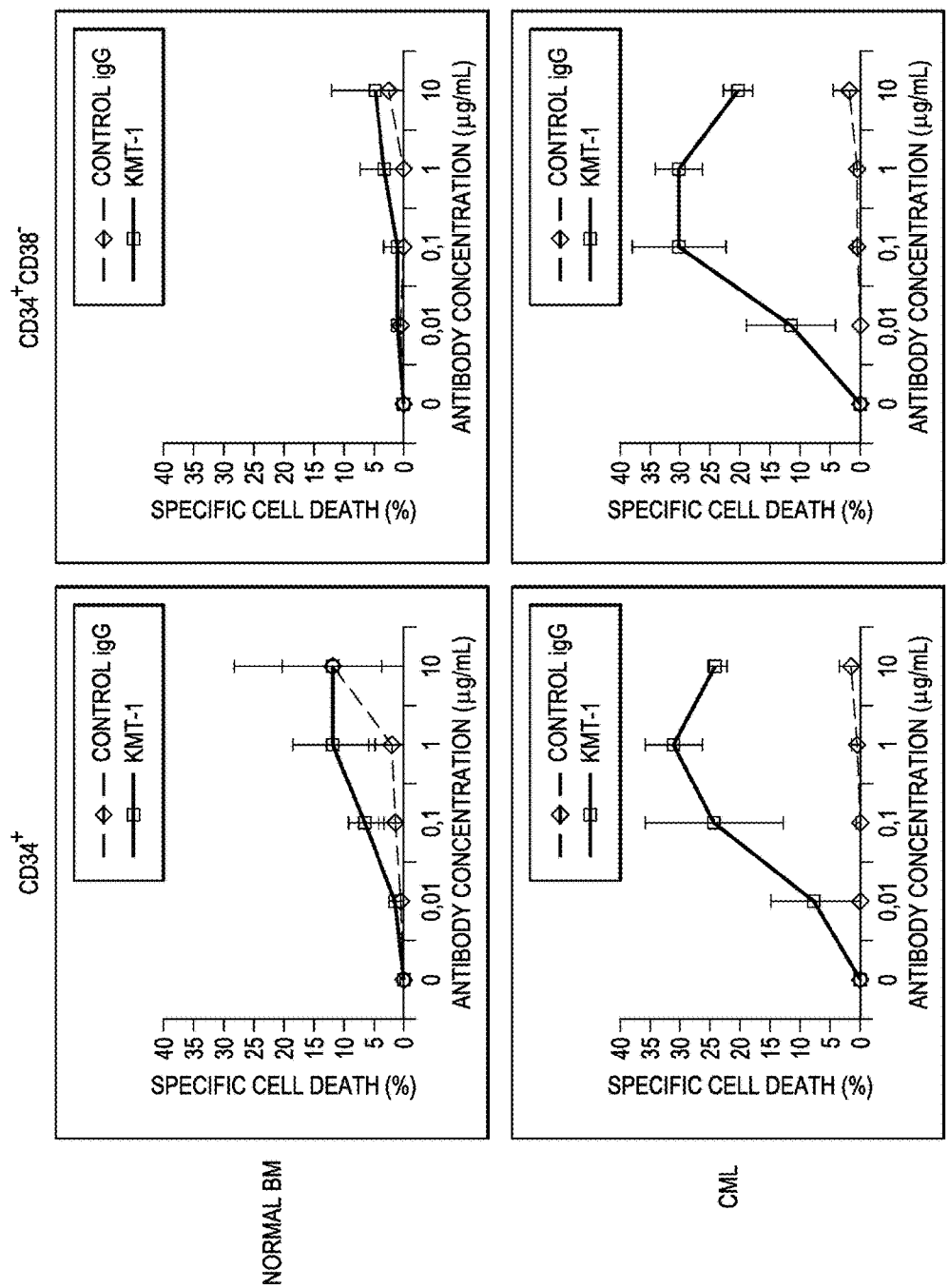

FIGS. 6A-B. Killing of CML Stem Cells by Antibody Targeting of IL1RAP

FIG. 6A shows the use of KMT-1, normal bone marrow CD34+CD38− cells stained negative for IL1RAP, whereas CML CD34+CD38+ and CD34+CD38− cells expressed IL1RAP. Histograms on CML-1 are shown from a representative experiment. White show control stained samples and gray show KMT-1 stained samples.

FIG. 6B shows that in, line with the level of IL1RAP expression, no obvious ADCC effect was seen using normal bone marrow CD34+CD38− cells, whereas KMT-1 induced a strong dose-dependent ADCC effect in both CML CD34+ and CD34+CD38− cells. As a control for unspecific ADCC effects, a rabbit IgG antibody was also used in the experiments. The graph shows the average and standard deviation of antibody induced cell death from three independent experiments using CML-1, CML-3, CML-4, and four normal bone marrow samples.

Figure 7A:
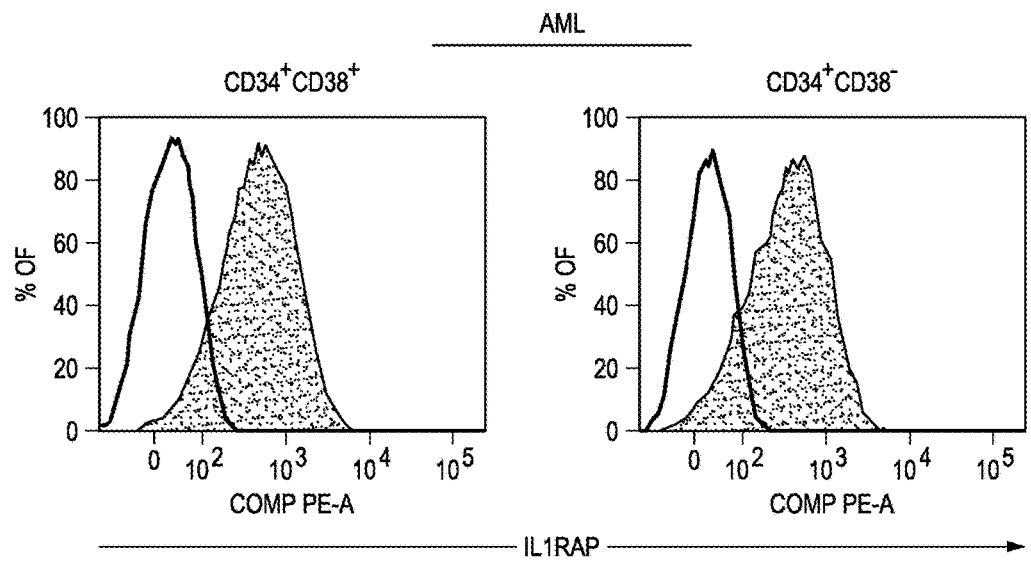
Figure 7B:
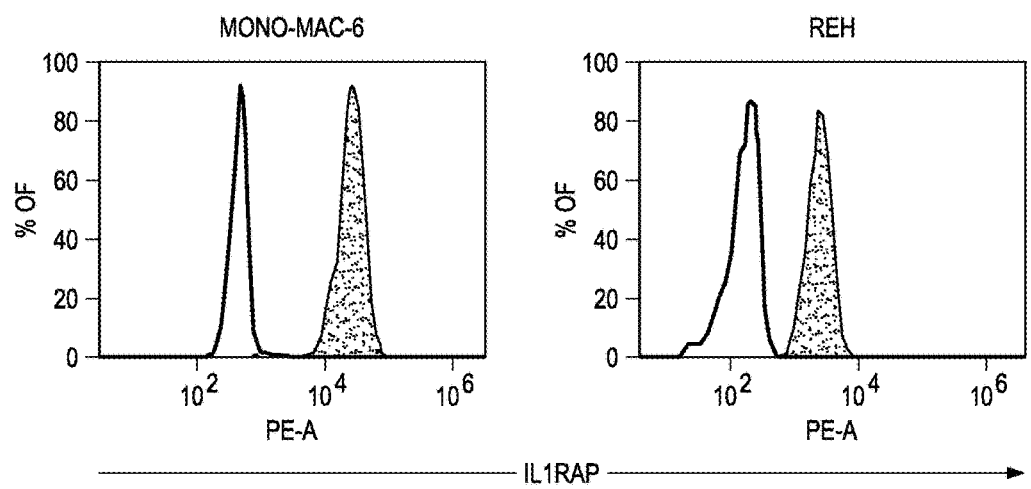
Figure 7C:
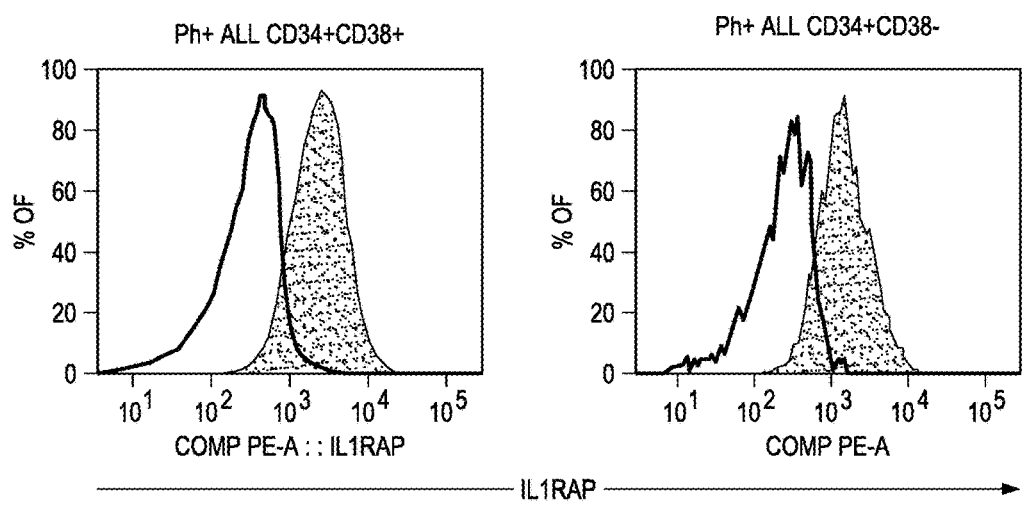

FIGS. 7A-C. IL1RAP is Expressed Also on Primary ALL and AML Stem Cells

In FIG. 7A, acute myeloid leukemia (AML) cells were received from patients at diagnosis. IL1RAP expression on CD34+CD38− and CD34+CD38+ cells from a representative AML patient is presented.

FIG. 7B shows that the AML cell line MONO-MAC-6 and the ALL cell line REH express IL1RAP.

In FIG. 7C, acute lymphoid leukemia (ALL) cells were received from patients at diagnosis. IL1RAP expression on CD34+CD38− and CD34+CD38+ cells from a representative Ph+ ALL patient is presented. White show control stained samples and gray show IL1RAP stained samples.

Figure 8:
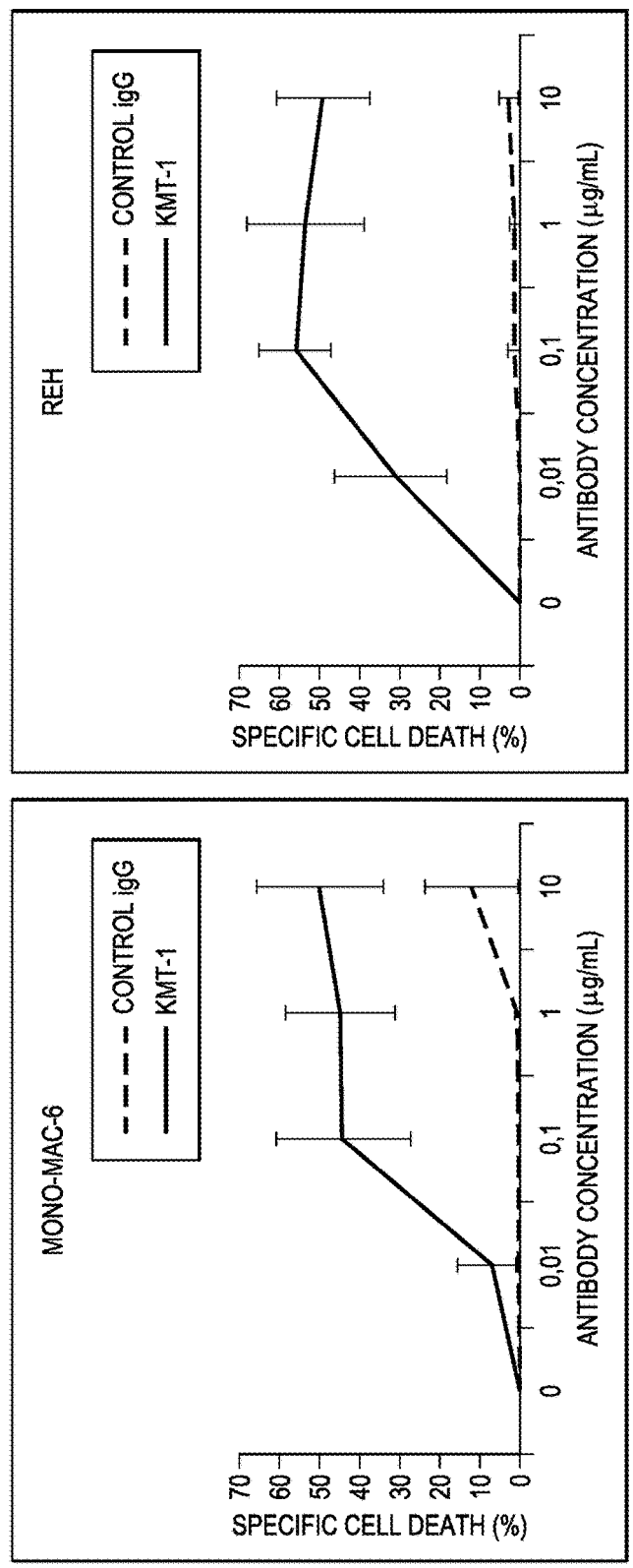

FIG. 8. Killing of AML and ALL Cell Lines by Antibody Targeting of IL1RAP

FIG. 8 shows, in ADCC assay, a KMT-1 dose dependent cell death was induced in both the MONO-MAC-6 and the REH cell line, suggesting that IL1RAP targeting antibodies may have a broader therapeutic window than just CML. As a control for unspecific ADCC effects, a rabbit IgG antibody was also used in the experiments. The graph shows the average and standard deviation of antibody induced cell death from three independent experiments.

Figure 9A:
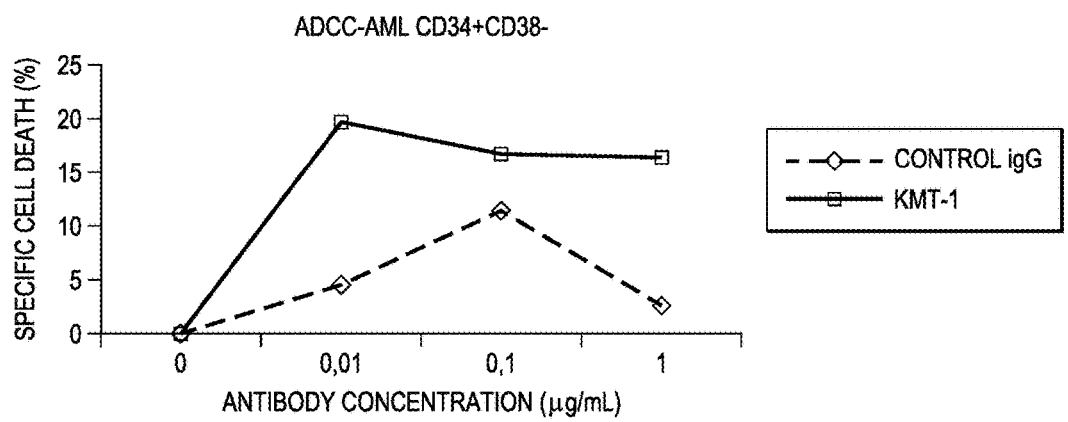
Figure 9B:
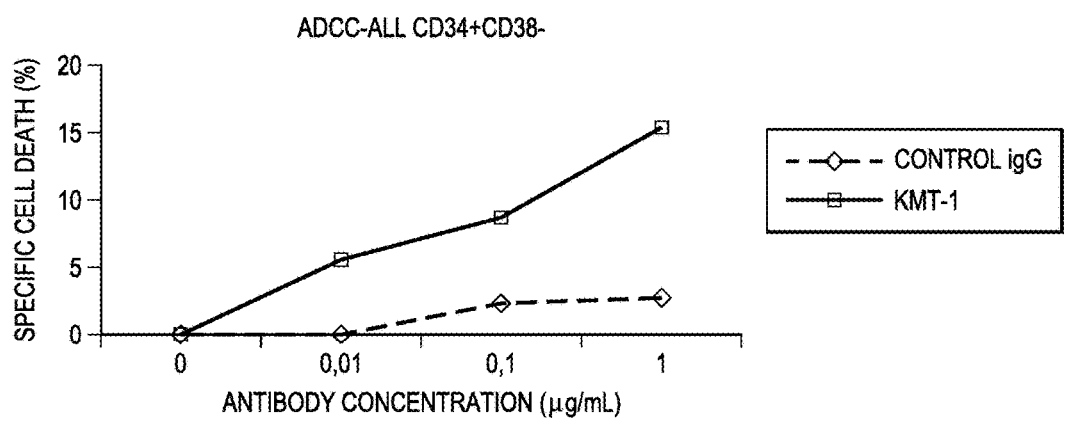

FIGS. 9A-B. Killing of AML and ALL Stem Cells by Antibody Targeting of IL1RAP

FIG. 9A shows that a KMT-1 induced cell death was observed in both primary AML CD34+CD38. and FIG. 9B shows ALL CD34+CD38– cells, confirming that IL1RAP targeting antibodies also have a therapeutic effect in AML and ALL with upregulation of IL1RAP on their cell surface. As a control for unspecific ADCC effects, a rabbit IgG antibody was also used in the experiments. The graph shows the specific antibody induced cell death.

Figure 10A:
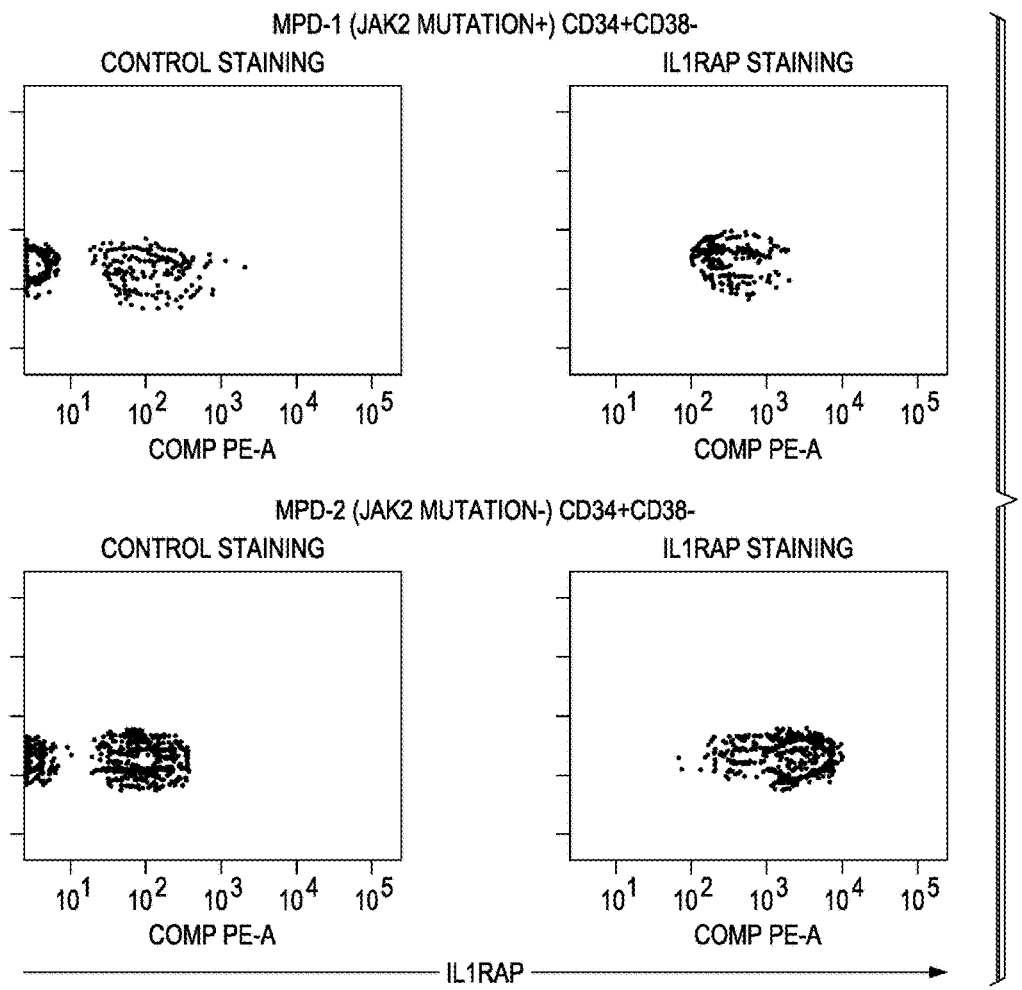
Figure 10B:
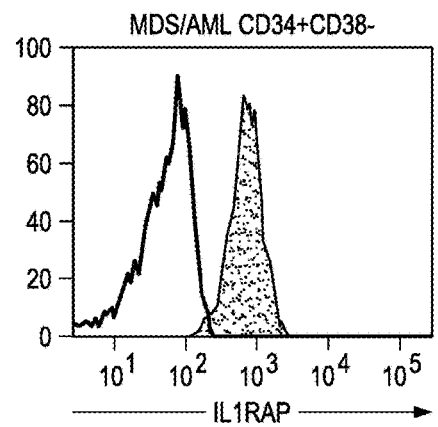

FIGS. 10A-B. IL1RAP is Expressed on Leukemic Stem Cells from MPD and MDS patients.

FIG. 10A shows contour plots showing IL1RAP expression in CD34+CD38– cells of two MPD patients (MPD-1 and MPD-2), with and without the JAK2 mutation.

FIG. 10B has histograms showing IL1RAP expression in an MDS patient progressed into AML. White show control stained samples and gray shows a sample stained with anti-IL1RAP antibodies.

EXAMPLE 1

IL1RAP is a Cell Surface Biomarker for Chronic Myeloid Leukemia Stem Cells

Summary

Therapeutic strategies for chronic myeloid leukemia (CML) aiming at achieving a permanent cure of the disorder, will require a full eradication of the CML stem cells. The CML stem cells, sharing the capacity to self-renew with normal hematopoietic stem cells (HSCs), represent a small population of leukemic cells that so far have been indistinguishable from normal (HSCs) using cell surface markers. One strategy to target the CML stem cell would be to identify a cell surface biomarker for CML stem cells, to which future therapeutic antibodies could be directed. In this study, we identified IL1RAP as commonly upregulated both in primitive CML CD34+ cells and as a consequence of ectopic P210 BCR/ABL1 expression using global gene expression analyses. We further show that IL1 RAP expression divides the rare CD34+CD38– cell population, harboring both CML and normal HSCs, into two fractions; one having low/absent expression, the other having higher IL1RAP expression. After establishing a protocol, allowing detection of BCR/ABL1 by FISH in small numbers of sorted cells, we observed that within the CML CD34+CD38– cells; the IL1RAP+ cells were BCR/ABL1+, whereas IL1RAP– cells were almost exclusively BCR/ABL1–. By further performing long term culture-initiating cell (LTC-IC) assays on the two cell populations, we found that candidate CML stem cells and normal HSC could be prospectively separated. This study thus identifies IL1RAP as the first cell surface biomarker distinguishing CML stem cells from normal HSC and opens up new avenues for therapeutic and diagnostic strategies in CML as well as in related disorders such as acute myeloid leukemia (AML), acute lymphoblastic leukemia (ALL), myeloproliferative disorders (MPDs) and myelodysplastic syndrome (MDS).

Introduction

To identify a cell surface biomarker for CML stem cells, we performed global gene expression analyses and identified the interleukin 1 receptor accessory protein (IL1RAP) as the top candidate, being upregulated both in primitive CML patient cells and as a consequence of ectopic P210 BCR/ABL1 expression. Upon development of an assay for detecting BCR/ABL1 in low numbers of sorted cells, we show that the IL1RAP expression enables prospective separation of primitive leukemic and normal cells. Through long-term culturing-initiating cell assays, we further show that IL1RAP is a cell surface biomarker for CML stem cells, for the first time allowing prospective separation of CML stem cells from normal HSC.

Material and Methods

Collection of CML Patient Cells

Isolation and Transduction of Cord Blood CD34+ Cells

Blood and occasionally bone marrow samples from CML patients were obtained at diagnosis before treatment was initiated after informed consent according to a protocol approved by the local ethical board. Samples were received both from the Department of Hematology at Lund University Hospital, Sweden and from Rigshospitalet, Copenhagen, Denmark. Mononuclear cells (MNCs) were separated using Lymphoprep™ (Axis-Shield PoC AS, Oslo, Norway) according to the manufacturer's instructions and CD34+ cells were enriched using the CD34+ cell isolation kit (Miltenyi Biotech, Bergisch Gladbach, Germany) as previously described[22], on a regular basis, this yielded a purity of CD34+ cells above 95%. A subfraction of mononuclear cells was viably stored in liquid nitrogen before antibody staining was initiated. CD34+ cells were split in two fractions; one fraction was washed in PBS and resuspended in Trizol and frozen in –80 C., whereas the other fraction was frozen in liquid nitrogen. As reference samples, bone marrow samples from healthy volunteers were obtained after informed consent at the Lund University Hospital, followed by CD34-cell isolation as described above.

Microarray Analysis

Microarray analysis was performed using oligonucleotide slides from the Swegene DNA Microarray Resource Center at Lund University, Sweden. Hybridizationss were performed using the Pronto Universal Hybridization kit (Corning Inc, Corning, N.Y.). The RNA isolation and microarray analysis was performed essentially as previously described[23]. Data visualization was performed using the software Qlucore Omics Explorer 2.0 (Qlucore, Lund, Sweden).

Flow Cytometric Analysis

Flow cytometric analyses were performed in a FACS Canto and flow cytometric cell sorting was done in a FACS Aria (both from BD). Prior to cell staining, CD34+ cells were thawed according to standard procedures and washed once in PBS containing 2% FCS (washing medium). Biotin-labeled goat anti-human IL1RAP polyclonal antibody (batch 667, R&D Systems, Abingdon, UK) was used at a 1:100 dilution for staining the cells for 30 min on ice. Subsequently, the cells were washed and PE-conjugated streptavidin was used at a 1:200 dilution for 30 min. The APC-conjugated anti-CD34 and FITC-conjugated anti-CD38 monoclonal antibodies were used for co-staining (except IL1RAP all antibodies used were purchased from Beckton-Dickinson Immunocytometry Systems, Mountain View, Calif.). Before cell sorting, cells were washed twice to avoid unspecific binding of PE-conjugated streptavidin. Isotype matching control antibodies were used as negative controls.

Cell Sorting and Interphase FISH

Glass slides were treated with 0.01% poly L-lysine (Sigma-Aldrich, Stockholm, Sweden) for two hours while kept in a moist chamber, washed once in water, and dried on a hot plate at 37° C. until dry. Subsequently, a hydrophobic pen (Daido Sangyo Co., Ltd. Tokyo, Japan) was used to draw circles with a 96-well tissue culture plate as template. Prior to cell sorting, but after at least two hours drying in room temperature, 25 µL PBS was applied to the rings to form drops. During cell sorting, 30 to 3000 cells were sorted simultaneously directly into two drops. To allow attachment of the cells to the surface and to avoid drying of the drops, slides were maintained in a moist chamber on ice for 30 min before cells were fixed in methanol:acetic acid (3:1) for 10 min. Subsequently, slides were incubated in a 70° C. oven over night, followed by FISH. Dual color probes for BCR/ABL1 (Abbot, Wiesbaden, Germany) were used.

Long Term Culture-initiating Cells (LTC-IC)

$M_2 10B_4$ stroma cells were cultured in RPMI-1640 medium supplemented with 10% FCS as previously described[24,25]. Two days prior to cell sorting, stroma cells were seeded into wells of a 96-well plate at density of 50,000 cells per mL in 200 µL Myelocult medium (Stem Cell Technologies, Vancouver, Canada) containing $10^{-6}$ M Hydrocortisone (Sigma-Aldrich, Stockholm, Sweden). Twenty-four hours before cell sorting, stroma cell were irradiated with 1000 Rad. During cell sorting, 100-500 cells were sorted directly into the stroma-precoated wells in duplicate and 100 µL medium was exchanged 3 h later. Once per week, the exchange of 100 µL culture medium was repeated. After 5-6 weeks culture, cells were washed and plated in methylcellusose medium (MethoCult H44435; Stem Cell Technologies) in a 24-well plate. Two weeks later, the number of colonies was scored. Colonies from individual wells were pooled, washed, applied to PBS drops on slides, and followed by FISH analysis as described above.

P210 BCR/ABL1 Expression in Cord Blood CD34+ Cells

Umbilical cord blood samples were collected from normal deliveries after obtaining informed consent according to a protocol approved by the local ethical board. CD34+ cells were enriched as previously described[22], yielding a purity of CD34+ cells above 95%. The RD114 pseudotyped MSCV-IRES-GFP (MIG) and MIG-P210 viral vectors were used in this study[23]. CD34+ cells were cultured and transduced in SFMM medium (Stem Cell Technology, Vancouver, Canada) supplemented with thrombopoietin (TPO; 50 ng/mL), stem cell factor (SCF; 100 ng/mL), and Flt-3-ligand (FL; 100 ng/mL) as previously described[23].

Results and Discussion

Global Gene Expression Analysis Identifies IL1RAP as Upregulated on CML CD34+ Cells Much effort has been put into investigations aimed at identifying a cell surface biomarker for Ph+ CML stem cells (reviewed by C Eaves[14]). Leukemic and normal cells can rather easily be identified retrospectively in CML following detection of the leukemia specific BCR/ABL1 fusion gene by FISH, making it an ideal disorder for evaluating attempts to prospectively separate leukemic and normal cells. However, so far, no cell surface marker has been identified that allows prospective separation of CML stem cells from normal HSC. Global gene expression analyses have proven to be a powerful strategy in searching for new HSC markers such as the SLAM receptors distinguishing hematopoietic stem and progenitor cells[15]. To search for upregulated genes encoding candidate cell surface biomarkers for CML stem cells, the transcriptional profiles of CD34+ cells from 11 CML patient samples and 5 normal bone marrow (bm) samples were compared. The identified upregulated genes in CML were matched to the Gene Ontology (GO) category "integral to plasma membrane" that had been manually curated to include all known CD molecules (see Material and Methods for details). In total, 13 upregulated genes in CML CD34+ cells matched to the integral to plasma membrane gene category (data not shown). To further link the upregulated genes more directly to P210 BCR/ABL1 expression, we in parallel generated a list of upregulated genes as a consequence of P210 BCR/ABL1 expression in cord blood CD34+ cells. This analysis resulted in 23 upregulated genes matching to the same GO category gene list (data not shown). Interestingly, only one gene, the Interleukin 1 receptor accessory protein (IL1RAP), showed a strong upregulation both in CD34+ CML cells and in cord blood CD34+ cells as a consequence of P210 BCR/ABL1 expression. The findings that IL1RAP was present on both gene lists suggest that its upregulation on primitive CML cells is closely coupled to the P210 BCR/ABL1 expression and indicate that IL1RAP is a novel leukemia-associated antigen on primitive CML cells.

IL1RAP is Upregulated on CD34+CD38− Cells from CML Patients and is Induced as a Consequence of Ectopic P210 BCR/ABL1 Expression IL1RAP is a member of the Toll-like receptor superfamily and is a well-known co-receptor to Interleukin 1 receptor type 1 (IL-1R1)[16]. IL1RAP is thus crucial in mediating the effect of the pro-inflammatory cytokine IL-1, but it is also involved in mediating the signal of IL-33, a cytokine that activates T-cells and mast cells through binding its receptor ST2, which subsequently dimerizes with IL1RAP[17]. IL-1R1 activation has previously been shown to stimulate colony growth of interferon sensitive CML cells[18], however, IL1RAP has to our knowledge not previously been linked directly to CML.

As P210 BCR/ABL1 is present in CML cells as a hallmark of the disease, ideally, a reliable cell surface biomarker in CML, should be directly coupled to the presence and expression of P210 BCR/ABL1. In agreement with the microarray data, IL1RAP expression was indeed upregulated on the cell surface on CB CD34+ cells following retroviral P210 BCR/ABL1 expression (FIG. 1). This suggests that P210 BCR/ABL1 regulates IL1RAP expression, either directly or through an indirect effect, strengthening its candidature as a CML biomarker.

We next investigated the cell surface IL1RAP expression on CML CD34+CD38+ cells, representing the majority and more mature CD34+ cells. In this cell population, an upregulation of IL1RAP was observed compared to the expression in corresponding normal bm cells (FIG. 2A, B). The normal CD34+CD38+ cells displayed a lower IL1RAP expression that partially overlapped with the expression on CML cells. We then turned to the CD34+CD38− cell compartment of normal cells, containing the HSCs. In agreement with a previous study, this population displayed a low/absent IL1RAP expression (FIG. 2C)[19]. Strikingly, the CD34+CD38− cells from CML patients, harboring both Ph+ CML stem cells and normal HSCs were divided into two populations; one having low/absent IL1RAP expression, the other having higher IL1RAP expression (FIG. 2C). In the peripheral blood (PB) of five CML patients, the IL1RAP positive cell fraction constituted between 75% and 95% of the CD34+CD38− cells (n=5). Based on these findings, we speculated that the IL1RAP expression might distinguish normal and leukemic cells within the CD34+CD38− cell compartment in CML. As all CML stem cells and normal HSC exclusively are found within the CD34$^+$CD38$^-$ cells, such separation between normal and leukemic cells, would allow a prospective separation of CML stem cells from normal HSC.

Flow-drop-FISH Shows that IL1RAP Expression Separates Normal and Leukemic Cells within CML CD34$^+$CD38$^-$ Cells To test whether the IL1RAP expression distinguishes normal (Ph$^-$) and leukemic (Ph$^+$) cells within the CML CD34$^+$CD38$^-$ cell compartment, we established a new protocol for doing fluorescent in situ hybridization (FISH) on small numbers of sorted cells (see Material and Methods). The first steps in this protocol is partly based on a method for sorting cells into drops on slides followed by single cell immuno-staining[20]. By applying this new protocol involving cell sorting directly into drops on slides followed by FISH, hereafter referred to as Flow-drop-FISH, we sorted as few as 30 cells into a drop, from which 15 nuclei were successfully scored by FISH (CML-5, FIG. 3). Interestingly, we found by Flow-drop-FISH that the CML CD34$^+$CD38$^-$IL1RAP$^+$ cells were BCR/ABL1$^+$, whereas CML CD34$^+$CD38$^-$ IL1RAP$^-$ cells were almost exclusively Ph$^-$ (n=5, FIG. 3). These data show that IL1RAP expression separates leukemic and normal cells within the CML CD34$^+$CD38$^-$ cell compartment, indicating that CML stem cells and normal HSC can be prospectively separated.

CML Stem Cells are CD34$^+$CD38$^-$IL1RAP$^+$ whereas Normal HSC are CD34$^+$CD38$^-$IL1RAP$^{-/low}$ Studies on chronic phase CML stem cells has so far relayed on access to rare CML patients in which the stem cells compartment have been dominated by leukemic cells following long-term assays[14]. As CML stem cells generally show poor engraftment in immuno-deficient mice, the long-term culture initiating cell (LTC-IC)-assay is widely used as a surrogate assay for detection of candidate CML stem cells. To test whether CML CD34$^+$CD38$^-$IL1RAP$^+$ and CD34$^+$CD38$^-$IL1RAP$^{-/low}$ uniquely contain candidate CML stem cells and normal HSC, respectively, we tested the two cell populations in the LTC-IC assay. For bone marrow CD34$^+$ cells from normal controls, long term culture-colony forming cells (LTC-CFC) were found at an >100-fold higher frequency among CD34$^+$CD38$^-$IL1RAP$^-$ cells compared to CD34$^+$CD38$^-$IL1RAP$^+$ cells (FIG. 4A, n=2), indicating that normal CD34$^+$CD38$^-$IL1RAP$^-$ are hierarchically on top of CD34$^+$CD38$^-$IL1RAP$^+$ cells. In CML, we observed on average a 3.6-fold higher frequency of LTC-CFC within the CD34$^+$CD38$^-$IL1RAP$^-$ cells compared to the CD34$^+$CD38$^-$IL1RAP$^+$ cells (n=5, FIG. 4A), suggesting that CML CD34$^+$CD38$^-$IL1RAP$^-$ cells are more enriched for primitive cells. Importantly, although a higher number of LTC-IC were found among CD34$^+$CD38$^-$IL1RAP$^-$ cells than within CD34$^+$CD38$^-$IL1RAP$^+$ cells from both CML patient samples and from normal controls, FISH on CML LTC-colonies revealed an almost complete discrimination between Ph$^-$ and Ph$^+$ cells in the two groups (FIG. 4B). CML LTC-colonies derived from CD34$^+$CD38$^-$IL1RAP$^-$ cells were almost exclusively Ph$^-$, whereas CD34$^+$CD38$^-$IL1RAP$^+$ were almost exclusively Ph$^+$. These data suggest that IL1RAP is a novel cell surface biomarker that can be used to separate CML stem cells from normal HSC.

Herein, we identified through global gene expression analysis a novel cell surface antigen, IL1RAP, that following challenging in multiple assays fulfilled the criteria for being a novel cell surface biomarker for Ph$^+$ CML stem cells. Based on this discovery, future directed therapies in CML could be designed to target the CML stem cells while preserving normal HSC by using a therapeutic antibody directed towards IL1RAP. In addition, an antibody cocktail containing anti-CD34, anti-CD38 and anti-IL1RAP antibodies can be used for diagnostic purposes and for follow-up studies of CML patients under different treatments. Importantly, a prospective separation of normal and CML stem cells will enable future mechanistic studies of these two cell populations. Moreover, we here also show that Flow-drop-FISH could serve as a useful method in characterizing genetic aberrations in small numbers of sorted cells, such as leukemic stem cells, a cell type that has been purified to increasingly smaller and purer cell populations[21]. For future studies, this method would for example allow detection of genetical aberrations in various small leukemic stem and progenitor cell populations, findings that are likely to provide novel insights into which orders the various aberrations have been acquired, key knowledge to understand leukemogenesis. In addition, Flow-drop-FISH could be used to monitor therapeutic effects on leukemic stem cells during treatment. Importantly, we here identified by using Flow-drop-FISH that IL1RAP is the first cell surface biomarker that distinguishes CML stem cells from normal HSCs, a finding that opens up new therapeutic opportunities for CML and other neoplastic hematologic disorders associated with upregulation of IL1RAP on stem cells and/or progenitor cells.

References

1. Deininger M W, Goldman J M, Melo J V. *The molecular biology of chronic myeloid leukemia. Blood.* 2000; 96:3343-3356.
2. Fialkow P J, Denman A M, Jacobson R J, Lowenthal M N. *Chronic myelocytic leukemia. Origin of some lymphocytes from leukemic stem cells. J Clin Invest.* 1978; 62:815-823.
3. Kavalerchik E, Goff D, Jamieson C H. *Chronic myeloid leukemia stem cells. J Clin Oncol.* 2008; 26:2911-2915.
4. Jiang X, Zhao Y, Smith C, et al. *Chronic myeloid leukemia stem cells possess multiple unique features of resistance to BCR-ABL targeted therapies. Leukemia.* 2007; 21:926-935.
5. Copland M, Hamilton A, Elrick L J, et al. *Dasatinib (BMS-354825) targets an earlier progenitor population than imatinib in primary CML but does not eliminate the quiescent fraction. Blood.* 2006; 107:4532-4539.
6. Jin L, Hope K J, Zhai Q, Smadja-Joffe F, Dick J E. *Targeting of CD44 eradicates human acute myeloid leukemic stem cells. Nat Med.* 2006; 12:1167-1174.
7. Tavor S, Petit I, Porozov S, et al. *CXCR4 regulates migration and development of human acute myelogenous leukemia stem cells in transplanted NOD/SCID mice. Cancer Res.* 2004; 64:2817-2824.
8. Jin L, Lee E M, Ramshaw H S, et al. *Monoclonal antibody-mediated targeting of CD123, IL-3 receptor alpha chain, eliminates human acute myeloid leukemic stem cells. Cell Stem Cell.* 2009; 5:31-42.
9. Majeti R, Chao M P, Alizadeh A A, et al. *CD47 is an adverse prognostic factor and therapeutic antibody target on human acute myeloid leukemia stem cells. Cell.* 2009; 138:286-299.
10. Hosen N, Park C Y, Tatsumi N, et al. *CD96 is a leukemic stem cell-specific marker in human acute myeloid leukemia. Proc Natl Acad Sci USA.* 2007; 104:11008-11013.
11. van Rhenen A, van Dongen G A, Kelder A, et al. *The novel AML stem cell associated antigen CLL-1 aids in discrimination between normal and leukemic stem cells. Blood.* 2007; 110:2659-2666.

12. Eisterer W, Jiang X, Christ O, et al. *Different subsets of primary chronic myeloid leukemia stem cells engraft immunodeficient mice and produce a model of the human disease. Leukemia.* 2005; 19:435-441.
13. Bhatia M, Wang J C, Kapp U, Bonnet D, Dick J E. *Purification of primitive human hematopoietic cells capable of repopulating immune-deficient mice. Proc Natl Acad Sci USA.* 1997; 94:5320-5325.
14. Jiang X, Zhao Y, Forrest D, Smith C, Eaves A, Eaves C. *Stem cell biomarkers in chronic myeloid leukemia. Dis Markers.* 2008; 24:201-216.
15. Kiel M J, Yilmaz O H, Iwashita T, Terhorst C, Morrison S J. *SLAM family receptors distinguish hematopoietic stem and progenitor cells and reveal endothelial niches for stem cells. Cell.* 2005; 121:1109-1121.
16. Subramaniam S, Stansberg C, Cunningham C. *The interleukin 1 receptor family. Dev Comp Immunol.* 2004; 28:415-428.
17. Ali S, Huber M, Kollewe C, Bischoff S C, Falk W, Martin M U. *IL-1 receptor accessory protein is essential for IL-33-induced activation of T lymphocytes and mast cells. Proc Natl Acad Sci USA.* 2007; 104:18660-18665.
18. Estrov Z, Kurzrock R, Wetzler M, et al. *Suppression of chronic myelogenous leukemia colony growth by interleukin-1 (IL-1) receptor antagonist and soluble IL-1 receptors: a novel application for inhibitors of IL-1 activity. Blood.* 1991; 78:1476-1484.
19. Hystad M E, Myklebust J H, Bo T H, et al. *Characterization of early stages of human B cell development by gene expression profiling. J Immunol.* 2007; 179:3662-3671.
20. Ema H, Morita Y, Yamazaki S, et al. *Adult mouse hematopoietic stem cells: purification and single-cell assays. Nat Protoc.* 2006; 1:2979-2987.
21. Dick J E. *Stem cell concepts renew cancer research. Blood.* 2008; 112:4793-4807.
22. Nilsson M, Karlsson S, Fan X. *Functionally distinct subpopulations of cord blood CD34$^+$ cells are transduced by adenoviral vectors with serotype 5 or 35 tropism. Mol Ther.* 2004; 9:377-388.
23. Jaras M, Johnels P, Agerstam H, et al. *Expression of P190 and P210 BCR/ABL1 in normal human CD34(+) cells induces similar gene expression profiles and results in a STAT5-dependent expansion of the erythroid lineage. Exp Hematol.* 2009; 37:367-375.
24. Hogge D E, Lansdorp P M, Reid D, Gerhard B, Eaves C J. *Enhanced detection, maintenance, and differentiation of primitive human hematopoietic cells in cultures containing murine fibroblasts engineered to produce human steel factor, interleukin-3, and granulocyte colony-stimulating factor. Blood.* 1996; 88:3765-3773.
25. Castor A, Nilsson L, Astrand-Grundstrom I, et al. *Distinct patterns of hematopoietic stem cell involvement in acute lymphoblastic leukemia. Nat Med.* 2005; 11:630-637.

EXAMPLE 2

Antibody-targeting of IL1RAP on Leukemia Stem and Progenitor Cells Cause Antibody-dependent Cell-mediated Cytotoxicity (ADCC)
Summary Therapeutic strategies for leukemias aimed at achieving a permanent cure will require a full eradication of the leukemia stem cells. The leukemia stem cells, representing a small population of leukemic cells, have so far have been indistinguishable from normal hematopoietic stem cells (HSCs) using cell surface markers. A new concept for targeting leukemia stem cells would be to identify a cell surface biomarker for leukemia stem cells, to which future therapeutic antibodies could be directed (see Example 1).

In this study, we generate an anti-IL1RAP antibody and provide proof of concept that anti-IL1RAP antibodies targeting chronic myeloid leukemia (CML) stem cells, Acute myeloid leukaemia (AML) stem cells, and Acute lymphoblastic leukaemia (ALL) stem cells can be used to induce antibody-dependent-cell-mediated cytotoxicity (ADCC), whereas no cytotoxic effect was observed on normal HSC. Furthermore, we demonstrate a dose-dependent IL1RAP targeting ADCC in the IL1RAP positive cell lines KU812 (CML), MONO-MAC-6 (acute myeloid leukemia; AML) and REH (acute lymphoblastic cell line; ALL). We also demonstrate that MDS and MPD stem cells have increased IL1RAP expression, indicative that future therapeutic anti-IL1RAP targeting antibodies will be effective also in these disorders.

This study thus opens up for a novel therapeutic opportunity in CML, AML, ALL, MDS, and MPD by antibody targeting of IL1RAP on leukemic stem cells.

Materials and Methods
Generation of KMT-1; a Polyclonal Rabbit Anti-human IL1RAP Antibody Rabbits were immunized with the extracellular domain of IL1RAP. Serum from rabbits were purified according to standard procedures, except that an additional step was added, in which antibodies binding to the immunoglobulin domain, present on the immunizing protein for increased half-life, was discarded through binding to immunoglobulin loaded columns. Purified antibodies were confirmed in ELISA to bind the extracellular domain of IL1RAP and to be devoid of antibodies binding the human immunoglobulin domain. When used in flow cytometry, a PE-conjugated goat anti-rabbit IgG antibody was used as secondary reagent.

ADCC Assay

The ADCC assay was based on a protocol previously described[1]. In brief, target cells were labelled with PKH26 (Sigma-Aldrich, St Louis, Mo.) according to manufacturer's instructions and either cells were put directly into wells of a 96-well plate, or seeded into the wells following sorting of CD34$^+$CD38$^-$ cells. The KU812 and KG-1 cell lines and primary CD34$^+$ cells were seeded at 10,000 cells per well, whereas primary CD34$^+$CD38$^-$ cells were seeded at 2,000-3,000 cells per well. Subsequently, antibodies were added to wells in different concentrations and incubated for 20 min before 100,000 NK-effector cells were added to each well. NK-cells were extracted from healthy volunteers after informed consent by using a NK-cell negative cell isolation kit according to manufacturer's instructions (Miltenyi Biotech, Bergisch Gladbach, Germany). Rabbit IgG antibodies purified from a non-immunized rabbit was used as control antibody in the experiments (R&D Systems Abingdon, UK). 7-AAD positive cells for detection of cell death were measured using a FACS CANTO flow cytometer (BD). The average and standard deviation of antibody induced cell death was calculated according to the following equation: (Percentage 7-AAD+ cells at defined antibody concentration—Percentage 7-AAD+ cells without antibody)/(0.01× Percentage 7-AAD− cells without antibody) from at least three independent experiments (except FIG. 9; 1 experiment only).

Samples from eleven AML patients and two Ph+ ALL patients were received from Lund University hospital and the expression of IL1RAP was analyzed in the CD34$^+$CD38+ and CD34$^+$CD38$^-$ cell populations using the same settings as for the analysis of CML cells. The AML cell line MONO-MAC-6 and the ALL cell line REH were also tested in ADCC assays using the same setup as the for the KG-1 and KU812 cell lines.

Results

Antibody-Targeting of IL1RAP on CML Stem and Progenitor Cells but Also on a CML Cell Line Directs NK-cells to ADCC Antibody-dependent-cell-mediated cytotoxicity (ADCC) is a conserved mechanism of the innate immune system, through which several therapeutic antibodies, such as Rituximab directed against CD20, are believed to at least partially exert their therapeutic effect[2]. To test whether ADCC could be achieved using IL1RAP as a target, we generated a polyclonal rabbit anti-human IL1RAP antibody hereafter referred to as KMT-1, as the Fc domain of rabbit antibodies in contrast goat antibodies are recognized by cells of the human immune system.

As expected, low levels of ADCC were observed in the IL1RAP negative/low leukemia cell line KG-1, even at high KMT-1 concentrations (FIG. 5 A, B). In contrast, in the CML cell line KU812 expressing IL1RAP, a natural killer (NK)-cell mediated ADCC was observed in the presence of KMT-1 (FIG. 5 A, B), demonstrating that KMT-1 has the potential to induce ADCC by recruiting cytotoxic immune cells to IL1RAP+ target cells.

On primary cells from CML patients and from normal controls, KMT-1 showed a slightly weaker, but similar staining pattern as the previously used polyclonal goat antihuman IL1RAP antibody (Example 1, FIG. 6A). Immature cells from CML-1, CML-3 and CML-4 (no more cells remained from CML-2 and CML-5) were tested in ADCC assays in parallel to cells from healthy control samples. In CML CD34$^+$ cells, the binding of KMT-1 resulted in ADCC at higher levels than in normal CD34$^+$ control cells, correlating to the expression level of IL1RAP, in particular at lower antibody concentrations (FIG. 6B). More strikingly, among the stem cell enriched CD34$^+$CD38$^-$ cells, KMT-1 did not induce ADCC of normal CD34$^+$CD38$^-$ cells, whereas a clear dose dependent ADCC effect was observed in CML CD34$^+$CD38$^-$ cells (FIG. 6 B), again showing strong correlation to the expression pattern of IL1RAP on these cell types.

Antibodies Targeting IL1RAP on AML and ALL Cells Direct NK-cells to ADCC

IL1RAP expression was observed in AML CD34$^+$CD38$^-$ cells in 9 out of 11 tested samples (FIG. 7A). In the CD34$^+$CD38$^+$ cell population, a similar IL1RAP expression pattern was observed (FIG. 7A). In addition, IL1RAP was expressed in the AML cell line MONO-MAC-6 and the ALL cell line REH (FIG. 7B). IL1RAP expression was also observed in Ph+ ALL CD34$^+$CD38$^-$ cells in 2 out of 2 tested samples (FIG. 7C). Using IL1RAP as target, the MONO-MAC-6 and REH cell lines were also tested in ADCC assays. In both these cell lines, a dose dependent IL1RAP targeting ADCC effect was observed (FIG. 8), demonstrating that therapeutic anti-IL1RAP targeting antibodies have a broader application than just CML.

We also performed ADCC experiments on primary AML and ALL CD34+CD38- cells and demonstrated proof of principle that also in these disorders, an increased cell death could be achieved using KMT-1 (FIG. 9).

In addition, CD34+CD38- cells from one MDS patient at progression into AML and two MPD patients (one of them JAK2 mutation+) were stained with an IL1RAP targeting antibody. An increased IL1RAP expression was observed in comparison to normal bone marrow CD34+CD38- cells (FIG. 10, FIG. 2C).

Discussion

In the present study, we have identified IL1RAP as the first cell surface biomarker that distinguishes candidate CML stem cells from normal HSCs and used this knowledge to induce an antibody-dependent cell killing of CML stem cells. Further, we identified IL1RAP as upregulated on AML stem cells, ALL stem cells, MPD stem cells and MDS stem cells and showed that both AML and ALL stem cells can be killed using an IL1RAP-targeting antibody, whereas normal stem cells were unaffected. Based on the finding that CML, ALL and AML stem cells can be killed by IL1RAP targeting antibodies, it is expected that also MPD and MDS stem cell would be killed in the ADCC assay. These findings opens up a new concept for treatments of leukemia patients by direct targeting of the leukemia stem cells, a concept that is distinct from the tyrosine kinase inhibitors currently used, which preferentially target cells downstream of the CML stem cells[3,4].

The reason why CML stem cells are resistant to drugs such as Glivec is partially unclear, but factors that may contribute are features such as quiescence and relatively high level of BCR/ABL1 expression, but also combinatorial expression of specific membrane transporter proteins in these cells[3,5,6]. Given these features of the CML stem cells, it is highly desirable to find novel treatment approaches to ultimately eradicate the CML stem cells. An antibody-based therapy directly targeting CML stem cells would serve in such a strategy as the antibodies mode of action is independent of the known resistant mechanisms causing CML stem cells to be unresponsive to kinase inhibitor treatments. The major limitations for such developments have been the complete lack of a cell surface receptor distinguishing CML Ph+ from normal, healthy (Ph-) stem cells. We herein identified IL1RAP as such a target from global gene expression analyses and importantly linked its expression to BCR/ABL1 expression (see Example 1 above).

Importantly, by generation of an antibody targeting IL1RAP, we here, for the first time, provide proof of concept that candidate CML stem cells can be targeted while preserving normal HSC. Importantly, as the antibodies mode of action in ADCC is to direct immunological cells to target cell killing, the therapeutic mechanisms is independent of the known mechanisms causing kinase inhibitor resistance in CML using current treatments. Hence, antibody targeting of CML stem cells has the capacity to eradicate CML stem cells, either alone or in combination with current regimens, ultimately leading to a permanent cure for CML patients.

Interestingly, we also observed that IL1RAP targeting antibodies can cause ADCC of AML stem cells; the most common type of acute leukemia among adults having a poor prognosis, and also ALL stem cells; the most common type of childhood leukemia. Collectively, the finding of IL1RAP expression on leukemic stem cells having a CD34$^+$CD38$^-$ immuno-phenotype in CML, AML, ALL, MDS, and MPD, and the ADCC experiments demonstrating cell killing in an IL1RAP dependent manner, indicates that these disorders can be treated with anti-IL1RAP therapeutic antibodies.

In the ADCC experiments presented herein, a polyclonal anti-human IL1RAP antibody was used (which is essentially a mixture of several different monoclonal antibodies). However, it will be appreciated by persons skilled in the art that individual monoclonal antibodies targeting IL1RAP can also be identified which have ADCC potential.

References
1. Wilkinson R W, Lee-MacAry A E, Davies D, Snary D, Ross E L. *Antibodydependent cell-mediated cytotoxicity: a flow cytometry-based assay using fluorophores. J Immunol Methods.* 2001; 258:183-191.
2. Morris J C, Waldmann T A. *Antibody-based therapy of leukaemia. Expert Rev Mol Med.* 2009; 11:e29.
3. Copland M, Hamilton A, Elrick L J, et al. *Dasatinib (BMS-354825) targets an earlier progenitor population than imatinib in primary CML but does not eliminate the quiescent fraction. Blood.* 2006; 107:4532-4539.
4. Jorgensen H G, Allan E K, Jordanides N E, Mountford J C, Holyoake T L. *Nilotinib exerts equipotent antiproliferative effects to imatinib and does not induce apoptosis in CD34+ CML cells. Blood.* 2007; 109:4016-4019.
5. Graham S M, Jorgensen H G, Allan E, et al. *Primitive, quiescent, Philadelphiapositive stem cells from patients with chronic myeloid leukemia are insensitive to STI571 in vitro. Blood.* 2002; 99:319-325.
6. Jiang X, Zhao Y, Smith C, et al. *Chronic myeloid leukemia stem cells possess multiple unique features of resistance to BCR-ABL targeted therapies. Leukemia.* 2007; 21:926-935.

The invention claimed is:

1. A method of treatment of leukemia, the method comprising administering a therapeutically effective amount of an antibody with specificity for an extracellular domain of the interleukin-1 receptor accessory protein (IL1RAP),
   wherein the antibody induces antibody-dependent cell-mediated cytotoxicity (ADCC) of pathological stem cells and/or progenitor cells expressing IL1RAP and being associated with the leukemia;
   wherein the antibody inhibits IL1RAP binding activity associated signaling on pathological stem cells and/or progenitor cells expressing IL1RAP.

2. The method according to claim 1, wherein the pathological stem cells and/or progenitor cells comprise a BCR/ABL1 fusion gene.

3. The method according to claim 1, wherein the leukemia is selected from the group consisting of chronic myeloid leukemia (CML), myeloproliferative disorders (MPD), myelodysplastic syndrome (MDS), acute lymphoblastic leukemia (ALL) and acute myeloid leukemia (AML).

4. The method according to claim 1, wherein the leukemia is CML.

5. The method according to claim 1, wherein the leukemia is MDP.

6. The method according to claim 1, wherein the leukemia is MDS.

7. The method according to claim 1, wherein the leukemia is ALL.

8. The method according to claim 1, wherein the leukemia is AML.

9. The method according to claim 1, wherein the pathological stem cells and/or progenitor cells comprise a Ph chromosome.

10. The method according to claim 1, wherein the antibody blocks binding of one or more co-receptors to IL1RAP.

11. The method according to claim 10, wherein the one or more co-receptors are selected from the group consisting of IL1R1, ST2, C-KIT and IL1RL2.

12. The method according to claim 1, wherein the antibody induces apoptosis of the stem cells and/or progenitor cells.

13. The method according to claim 1, wherein the antibody further comprises a cytotoxic moiety.

14. The method according to claim 1, wherein the antibody blocks binding of IL1R1.

* * * * *